(12) United States Patent
Smit et al.

(10) Patent No.: US 7,270,993 B2
(45) Date of Patent: Sep. 18, 2007

(54) **PROTEASE DEFICIENT *CAULOBACTER* HOST CELLS**

(75) Inventors: John Smit, Richmond (CA); John F. Nomellini, Richmond (CA); Wade H. Bingle, Vancouver (CA)

(73) Assignee: The University of Bristish Columbia, Vancouver, British Columbia (CA)

( * ) Notice: Subject to any disclaimer, the term of this patent is extended or adjusted under 35 U.S.C. 154(b) by 375 days.

(21) Appl. No.: 10/478,676

(22) PCT Filed: May 22, 2002

(86) PCT No.: PCT/CA02/00722

§ 371 (c)(1),
(2), (4) Date: May 27, 2004

(87) PCT Pub. No.: WO02/095039

PCT Pub. Date: Nov. 28, 2002

(65) Prior Publication Data

US 2005/0032194 A1    Feb. 10, 2005

(30) Foreign Application Priority Data

May 22, 2001  (CA) .................................. 2347657

(51) Int. Cl.
*C12N 15/00* (2006.01)
*C12N 15/57* (2006.01)
*C12N 15/62* (2006.01)
*C12N 1/21* (2006.01)
*C12Q 1/02* (2006.01)

(52) U.S. Cl. .................. 435/252.4; 435/4; 435/7.32; 435/29; 435/30; 435/69.1; 435/320.1; 435/440; 536/23.2

(58) Field of Classification Search ............ None
See application file for complete search history.

(56) References Cited

U.S. PATENT DOCUMENTS

| 5,500,353 | A  | * | 3/1996  | Smit et al. ............... 435/69.1  |
| 5,976,864 | A  | * | 11/1999 | Smit et al. ............... 435/252.3 |
| 6,210,948 | B1 | * | 4/2001  | Smit et al. ............... 435/252.3 |
| 6,368,599 | B1 | * | 4/2002  | Langermann et al. .... 424/184.1 |
| 6,423,538 | B1 | * | 7/2002  | Wittrup et al. ........... 435/320.1 |
| 2002/0009792 | A1 | * | 1/2002 | Smit et al. ............... 435/252.3 |
| 2003/0135037 | A1 | * | 7/2003 | Smit et al. ............... 536/23.72 |

OTHER PUBLICATIONS

Nierman et al., "*Caulobacter crescentus* CB15 Section 76 of 359 of the Complete Genome", Database EMBL, (Mar. 22, 2001).
Bingle et al., "Linker Mutagenesis of the *Caulobacter crescentus* S-Layer Protein: Toward a Definition of an N-Terminal Anchoring Region and a C-Terminal Secretion Signal and the Potential for Heterologous Protein Secretion", Journal of Bacteriology, American Society for Microbiology, vol. 179, No. 3, pp. 601-611. (1997).

* cited by examiner

*Primary Examiner*—Kathleen Kerr Bragdon
*Assistant Examiner*—William W. Moore
(74) *Attorney, Agent, or Firm*—Scully, Scott, Murphy & Presser, P.C.

(57) ABSTRACT

*Caulobacter* optimized for use in expression of heterologous peptides as part of a hybrid *Caulobacter* S-layer protein are provided as well as methods for producing such *Caulobacter*. *Caulobacter* of this invention are deficient in a native *Caulobacter* protease that cleaves hybrid S-layer proteins. Also provided are *Caulobacter* libraries and methods for sorting such libraries using cell sorting technology such as FACS.

26 Claims, 5 Drawing Sheets

5' region of sap (~ 1kb)

3' region of sap (~ 1kb)

1 2 3 4

A    ← RsaA
        98 kDa

← RsaA (485/IHNVG20)
        cleavage products
        2 x 50 kDa

B    ← Intact RsaA
        (485/IHNVG20)
        100 kDa

← RsaA (485/IHNVG20)
        cleavage products
        2 x 50 kDa

C    ← RsaA or intact
        RsaA (485/IHNVG20)
        98 or 100 kDa

← RsaA (485/IHNVG20)
        cleavage products
        2 x 50 kDa

Figure 4

PROTEASE DEFICIENT *CAULOBACTER* HOST CELLS

This application is the §371 national phase of International Application PCT/CA02/00722, filed May 22, 2002, which claims priority from Canadian Application 2,347,657, filed on May 22, 2001.

BACKGROUND OF THE INVENTION

The gram-negative bacterium *Caulobacter* elaborates a paracrystalline protein surface layer (S-layer) which covers the surface of its outer membrane (Smit, et al., 1981; 1992). The S-layer protein monomer is secreted by a Type I secretion mechanism relying upon a C-terminal secretion signal which remains attached to the rest of the protein during the secretion process (Gilchrist, et al., 1992; Bingle, et al. 1997a; and, Awram and Smit 1998). Once the protein monomer is secreted, the S-layer forms by a process of self-assembly as a hexagonal array of about 40,000 interlinked protein monomers (Nomellini, et al., 1997). Anchoring of the S-layer protein to the cell surface is dependent on a smooth lipopolysaccharide (LPS) molecule and $Ca^{+2}$ ions (Walker, et al, 1994) and involves the N-terminal portion of the S-layer monomer (Bingle, et al, 1997 a,b). The abundance, cell-surface location and geometrical packing of the S-layer protein as well as the inherent properties of *Caulobacter* (ease of genetic manipulation, simple growth requirements, non-pathogenic nature, and biofilm-forming characteristics) have led to the exploitation of the *Caulobacter*/S-layer system for biotechnology development (Smit, et al., 2000).

Through use of gene fusions encoding the C-terminal secretion signal of the S-layer monomer linked to sequences encoding a heterologous peptide, the *Caulobacter*/S-layer system is capable of secreting large quantities of the heterologous peptide (PCT patent applications published under No. WO 97/34000 and WO 00/49153; and, Bingle, et al., 2000). Such *Caulobacter* expression systems are available commercially under the trade name PurePro™ (Invitrogen, Carlsbad, Calif.). The PureProm™ system is designed for expression of "C-terminal hybrid proteins" in which a heterologous peptide is linked to the S-layer monomer C-terminal secretion signal and does not form an S-layer on the host.

The *Caulobacter*/S-layer system is also used for expression of heterologous peptides inserted into sites within a full-length (or nearly full-length) S-layer monomer resulting in production of what is termed herein "full-length hybrid protein". In such cases, a sufficient portion of the N-terminal region of the S-layer monomer is present to provide anchoring of the hybrid protein to the cell surface. The C-terminal secretion signal is present to permit secretion of the hybrid protein. Various preferred sites for insertion of heterologous peptides into the S-layer protein have been reported (WO 97/34000; and, Bingle, et al., 1997(b)). The hybrid S-layer protein so produced is capable of self-assembly on the cell surface resulting in an array of hybrid S-layer protein monomers forming as an S-layer on the cell surface. In this manner, heterologous peptides may be expressed and presented on the cell surface. This technology has particular use in expression and presentation of antigens.

A phenomenon observed during the development of the *Caulobacter*/S-layer system was the apparent proteolytic cleavage of various hybrid proteins. This was initially observed for both C-terminal hybrid proteins and full-length hybrid proteins. No obvious site specificity was associated with this phenomenon despite monitoring the degradation of numerous modified S-layer proteins comprising different heterologous peptides of varying lengths inserted at different places in the S-layer protein monomer (Bingle, et al. 1997a, b) it has now been reported (Simion, B. et al. 2001) that smaller proteins seen contaminating preparations of C-terminal hybrid proteins are not the result of proteolytic activity but rather the result of internal translation initiation following Met residues within the heterologous or "passenger" portion of the hybrid protein. Nevertheless, the cleavage phenomenon still places limitations on the use of *Caulobacter* as an expression system for full length hybrid proteins, particularly when the "passenger" peptide is unknown or uncharacterized, since it would then be difficult to know if this phenomenon has affected the hybrid product.

The use of a biological system to express and display a panel or library of different peptides to assess the ability of the peptides to bind to a chosen target, has become a powerful tool for investigating interaction of cellular components (see U.S. Pat. Nos. 5,223,409 & 5,571,698). In this methodology, nucleic acids each encoding a different peptide plus a signal for display of the peptide on the outer surface of a biological system, are introduced into the system. The peptides are expressed and binding domains in the peptides are displayed on the outer surface of the biological system. The system is exposed to target molecules and those members of the system which bind target molecules are isolated and the nucleic acids amplified. Successful binding domains are then characterized. This general method of exposing a variety of peptides, each displaying a different putative binding region, is termed "panning" herein. To date, phage is the preferred biological system for use in panning methodologies. This is partly due to difficulties in the use of bacterial systems for expression and display of heterologous peptides.

SUMMARY OF THE INVENTION

It has now been discovered using studies involving full-length hybrid proteins that a protease is synthesized by *Caulobacter* with an unusual structural feature: the enzyme possesses a domain sharing sequence similarity with the S-layer protein monomer. This native protease is responsible for the cleavage phenomenon seen with *Caulobacter* expressing heterologous peptides inserted into a full-length S-layer protein.

This discovery provides the means for optimizing use of *Caulobacter* as a system for expression and cell-surface display of heterologous peptides and for use of such a system for expression of unknown or uncharacterized peptides with good fidelity. This facilitates the use of *Caulobacter* as an expression system for producing random libraries of peptides or gene fragments for display and panning purposes. The methodologies known in the art for expression of heterologous peptides within an S-layer monomer followed by assembly and adherence of hybrid S-layer protein on a *Caulobacter* cell surface may now be used in a bacterial-mediated library display system. This has significant advantages over conventional phage display, notably because *Caulobacter* are of a sufficient size to be sorted through use of conventional cell sorting techniques such as fluorescent activated cell sorting (FACS). Such techniques cannot be used for sorting phage.

This invention provides an isolated *Caulobacter* deficient in a protease native to *Caulobacter* that cleaves hybrid *Caulobacter* S-layer protein monomers. Also provided is a library of such *Caulobacter* in which members of the library differ by the amino acid sequence of heterologous peptides in hybrid S-layer protein monomers expressed by the members.

This invention also provides a method of producing a *Caulobacter* optimized for use as a host cell for expression of a hybrid *Caulobacter* S-layer protein monomer, comprising: i) providing a *Caulobacter* which exhibits protease activity whereby hybrid S-layer protein monomers expressed by the *Caulobacter* are cleaved; ii) mutating the *Caulobacter*; and iii) selecting and culturing a mutated *Caulobacter* which does not exhibit said activity. Mutation may be by insertion, deletion, or substitution and may be performed through use of radiation and/or chemical mutagens, transposon insertion, homologous recombination or other methods. Also provided are mutated *Caulobacter* or descendents thereof produced by this method and libraries of such *Caulobacter*.

The native *Caulobacter* protease cleaves hybrid S-layer protein monomers as defined herein, in preference to wild-type S-layer protein monomers. The protease appears to be specific for S-layer protein monomers. Within this context, the protease appears to have general specificity for cleavage of hybrid S-layer protein monomers, but tends to cleave C-terminal of Arg and Phe residues. The protease may comprise one or more RTX sequences characteristic of known calcium binding consensus sequences and metalloprotease active site comprising a sequence characteristic of a metalloprotease active site consensus sequence. In this specification, the native *Caulobacter* protease is termed "Sap", an acronym for "S-layer associated protease". In this specification, a gene encoding this protease is termed "sap".

The Sap protease may comprise a C-terminal portion of about 150 to about 250, preferably about 190 to about 230, and more preferably about 200 amino acids having about 30% or more sequence identity to a portion of the amino acid sequence of a *Caulobacter* S-layer protein monomer, as determined using the Blast™ search algorithm at default settings (see: Altschul, S. F., et al. 1997). The protease may comprise from about 600 to about 700 amino acids, preferably about 630 to about 670 amino acids, and more preferably about 650 to about 660 amino acids, depending upon the source strain. Sap protease sequences described herein have about 658 amino acids. The portion of a *Caulobacter* S-layer protein monomer to which the protease exhibits sequence identity will be of similar size to the protease C-terminal portion and will be located toward the N-terminus of the S-layer protein monomer. A portion of an S-layer protein monomer exhibiting sequence identity as described above includes amino acids 23-242 of RsaA. A region of the protease exhibiting such sequence identity to RsaA may be a region corresponding to amino acids 451-650 of the specific Sap amino acid sequence described herein. The protease may further comprise an N-terminal region exhibiting about 50% or more sequence identity (determined as described above) with a *P. aeruginosa* alkaline protease region, as described below. The protease may comprise an amino acid sequence that has about 75%, 80%, 85%, 90%, 95% or more sequence identity to the specific Sap amino acid sequence disclosed herein.

This invention provides *Caulobacter* in which a native protease as described above is not expressed or is inactive (a "protease-negative" strain). These *Caulobacter* may comprise a mutated gene or coding region for the native protease. Protease-negative strains of this invention may also comprise recombinant DNA operably linked to a promoter recognized by *Caulobacter*, wherein the recombinant DNA comprises a nucleic acid sequence encoding at least a C-terminal secretion signal of *Caulobacter* S-layer protein monomer. The recombinant DNA may further comprise a nucleic acid sequence encoding sufficient part of *Caulobacter* S-layer protein monomer N-terminal region to provide for attachment of the coding product of the recombinant DNA to the cell surface of the *Caulobacter*. The recombinant DNA may comprise substantially all of a *Caulobacter* S-layer protein gene. The DNA may further comprise restriction sites to facilitate insertion of DNA encoding one or more peptides (including polypeptides and proteins) heterologous to *Caulobacter* S-layer protein into the recombinant DNA whereby the recombinant DNA encodes a hybrid S-layer protein monomer comprising all or part of an S-layer protein monomer and the one or more heterologous peptides. The recombinant DNA may further comprise DNA encoding a peptide, polypeptide, or protein heterologous to *Caulobacter* S-layer protein monomer. The recombinant DNA may be present in the *Caulobacter* on a plasmid or integrated into the *Caulobacter* genome.

This invention provides a panel or library of *Caulobacter* wherein individual members of the panel or library express different heterologous peptides, polypeptides, or proteins as part of a hybrid S-layer protein monomer, as described above. Preferably, the *Caulobacter* in the panel or library will be one or more protease-negative strains of this invention. Also provided are methods of sorting such a library according to whether a target to which the library is exposed binds to hybrid S-layer protein monomers on members of the library.

This invention also provides methods for detecting binding of a target compound to the surface of a *Caulobacter* that is a member of a library or panel as described above. Preferably, the target compound will be labelled, preferably with a fluorescent label. Detection of members of the panel or library to which the compound is bound may be done by FACS and performed by a flow cytometer. These methods may further comprise selection of *Caulobacter* to which the target binds, amplification of DNA encoding the heterologous peptide, polypeptide, or protein and sequencing of said DNA.

This invention provides a method of sorting members of a *Caulobacter* library according to ability of S-layer on a *Caulobacter* to bind to a target, wherein members of the library express and secrete different hybrid S-layer protein monomers, comprising: i) exposing the library to a fluorescent labelled target; and ii) segregating members of the library with a flow cytometer according to whether the labelled target is bound to a member or is not bound to a member.

BRIEF DESCRIPTION OF THE DRAWINGS

FIG. 4: a copy of a SDS-PAGE gel showing analysis of RsaA(485/IHNVG20) synthesized by Sap⁺ and Sap⁻ strains of *C. crescentus*. The protein was extracted from the cell-surface by the "low-pH" method. The region of the gels containing the 26 kDa fragment is not shown. A. Proteolytic cleavage of RsaA and RsaA (485/IHNVG20) in Sap⁺ JS4000. Lanes: 1, Low pH extract of JS4000; 2, Low pH extract of (pWB9KSAC:rsaAΔP[485/IHNVG20]); 3, Low pH extract of JS4000 (pWB9KSAC:rsaAΔP). B. Proteolytic cleavage of RsaA (485/IHNVG20) in Sap⁺ JS4020 and Sap⁻ Tn5 mutant JS4021. Lanes: 1, JS4020; 2, JS4021; 3, JS4021 (pBBR1MCS:Kmsap). C. Complementation of the UV/NTG mutation in Sap⁻ JS4015 containing either pWB9KSAC:rsaAΔP or pWB9KSAC:rsaAΔP [485/IHNVG20]). Lanes: 1, Cleavage of RsaA (485/IHNVG20) in Sap⁻ JS4015; 2, Cleavage of RsaA in Sap⁻ JS4015; 3, Cleavage of RsaA (485/IHNVG20) in Sap⁺ JS4015 (pBBR1MCS:Kmsap); 4, Cleavage of RsaA in Sap⁺ JS4015 (pBBR1MCS:sap).

DETAILED DESCRIPTION OF THE INVENTION

Figure 1:
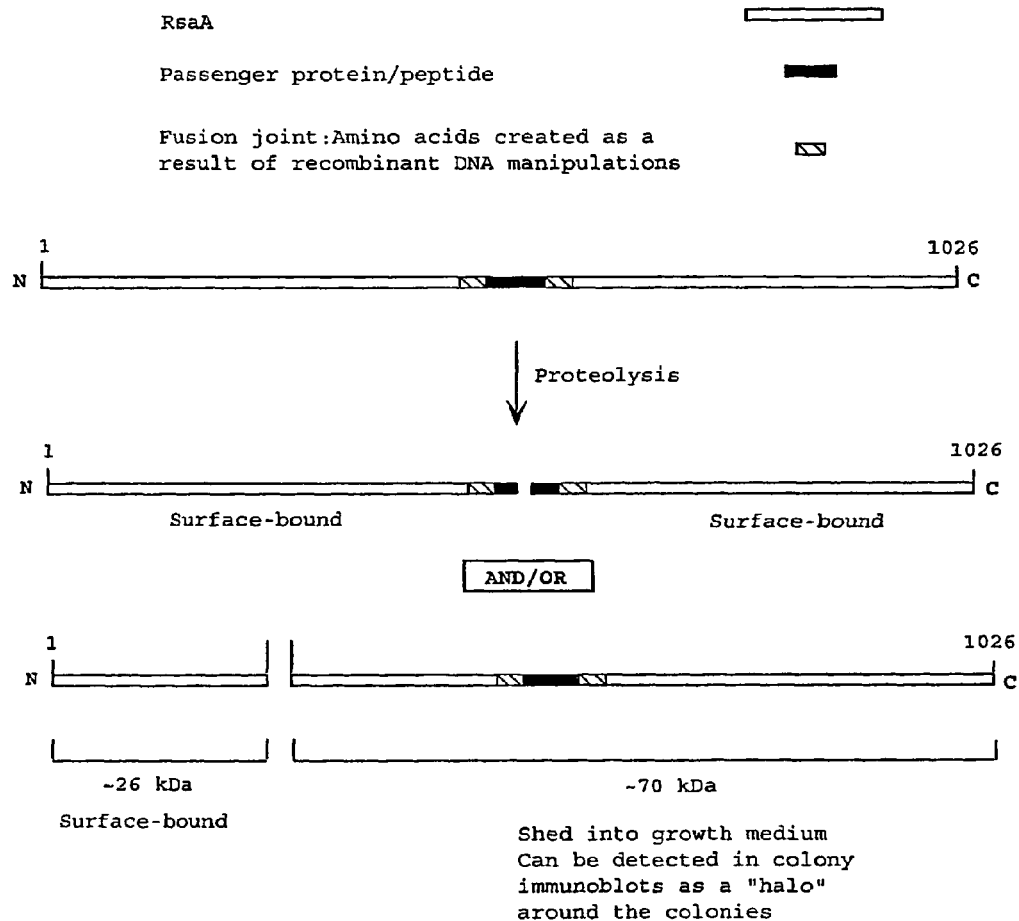
FIG. 1: a schematic diagram of the "proteolytic phenotype" associated with the expression of full-length RsaA hybrid proteins.
Figure 2:
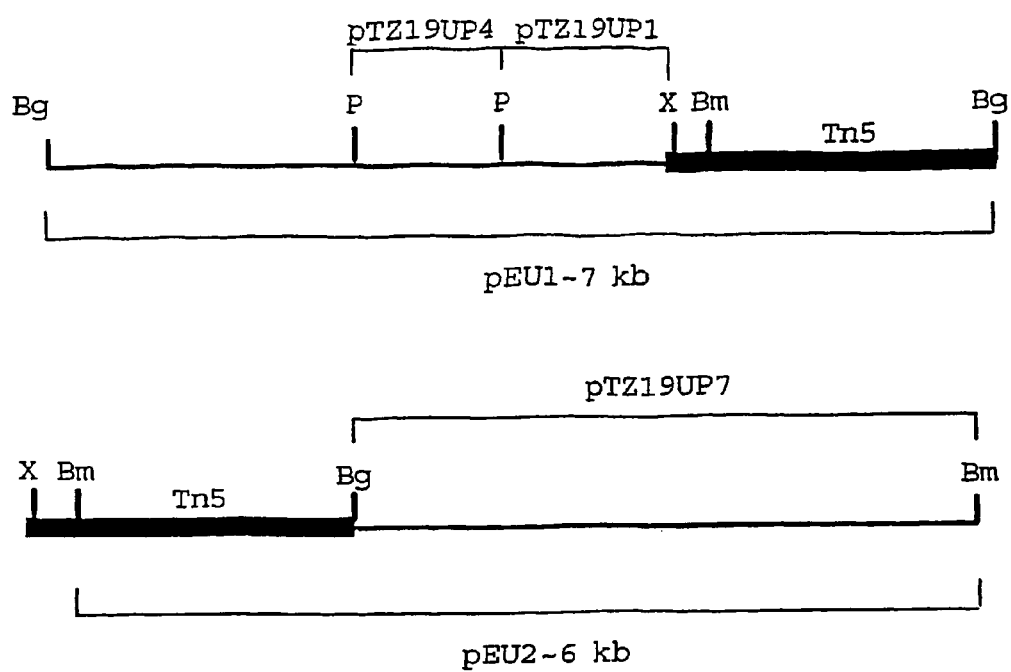
FIG. 2: a schematic representation of plasmids containing Tn5 interruptions of DNA encoding the *Caulobacter* protease (Sap).
Figure 3:
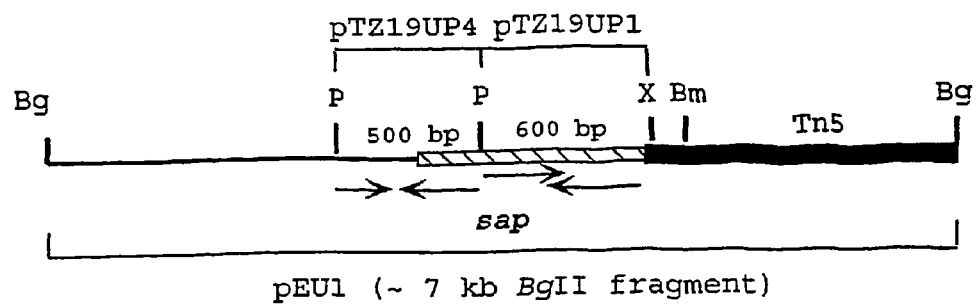
FIG. 3: a schematic showing location and orientation of Tn5 insertion in the protease (sap) gene of *C. crescents* JS4020 and nucleotide sequencing of the Tn5 interrupted gene. Arrows indicate regions of *Caulobacter* DNA subjected to nucleotide sequencing in plasmids pTZ19Up 1, 4 and 7. Abbreviations for restriction sites: Bm: BamHI; Bg: Bg/II; P: PstI; X: XbaI.
Figure 3:
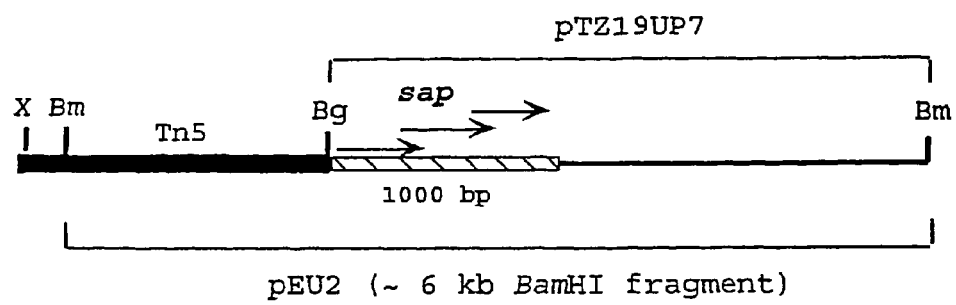

In this specification, the terms "S-layer protein monomer" and "S-layer protein" refer to a protein typically expressed by wild-type *Caulobacter* and which forms an S-layer on the cell surface of the *Caulobacter*. Representative of these S-layer protein monomers is RsaA, the S-layer protein monomer of *C. crescentus*. The amino acid sequence of RsaA is known and is also shown in Table 1 (SEQ ID NO: 1). The latter sequence may serve as a reference for identifying S-layer protein monomers of different strains and species of *Caulobacter* or as a reference for identifying the *Caulobacter* protease described herein through sequence comparison. The numbering of amino acid residues of RsaA referred to herein corresponds to the residue numbering in Table 1. The sequence of the native gene encoding RsaA is known and is termed "rsaA".

TABLE 1

RsaA amino acid sequence (SEQ ID NO: 1; Genbank Accession No. AAC38665). The rsaA gene sequence is at Genbank Accession No. AF062345.

| | | | | |
|---|---|---|---|---|
| 1 MAYTTAQLVT | AYTNANLGKA | PDAATTLTLD | AYATQTQTGG | LSDAAALTNT LKLVNSTTAV |
| 61 AIQTYQFFTG | VAPSAAGLDF | LVDSTTNTND | LNDAYYSKFA | QENRFINFSI NLATGAGAGA |
| 121 TAFAAAYTGV | SYAQTVATAY | DKIIGNAVAT | AAGVDVAAAV | AFLSRQANID YLTAFVRANT |
| 281 PFTAAADIDL | AVKAALIGTI | LNAATVSGIG | GYATATAAMI | NDLSDGALST DNAAGVNLFT |
| 241 AYPSSGVSGS | TLSLTTGTDT | LTGTANNDTF | VAGEVAGAAT | LTVGDTLSGG AGTDVLNWVQ |
| 301 AAAVTALPTG | VTISGIETMN | VTSGAAITLN | TSSGVTGLTA | LNTNTSGAAQ TVTAGAGQNL |
| 361 TATTAAQAAN | NVAVDGGANV | TVASTGVTSG | TTTVGANSAA | SGTVSVSVAN SSTTTTGAIA |
| 421 VTGGTAVTVA | QTAGNAVNTT | LTQADVTVTG | NSSTTAVTVT | QTAAATAGAT VAGRVNGAVT |
| 481 ITDSAAASAT | TAGKIATVTL | GSFGAATIDS | SALTTVNLSG | TGTSLGIGRG ALTATPTANT |
| 541 LTLNVNGLTT | TGAITDSEAA | ADDGFTTINI | AGSTASSTIA | SLVAADATTL NISGDARVTI |
| 601 TSHTAAALTG | ITVTNSVGAT | LGAELATGLV | FTGGAGADSI | LLGATTKAIV MGAGDDTVTV |
| 661 SSATLGAGGS | VNGGDGTDVL | VANVNGSSFS | ADPAFGGFET | LRVAGAAAQG SHNANGFTAL |
| 721 QLGATAGATT | FTNVAVNVGL | TVLAAPTGTT | TVTLANATGT | SDVFNLTLSS SAALAAGTVA |
| 781 LAGVETVNIA | ATDTNTTAHV | DTLTLQATSA | KSIVVTGNAG | LNLTNTGNTA VTSFDASAVT |
| 841 GTGSAVTFVS | ANTTVGEVVT | IRGGAGADSL | TGSATANDTI | IGGAGADTLV YTGGTDTFTG |
| 901 GTGADIFDIN | AIGTSTAFVT | ITDAAVGDKL | DLVGISTNGA | IADGAFGAAV TLGAAATLAQ |
| 961 YLDAAAAGDG | SGTSVAKWFQ | FGGDTYVVVD | SSAGATFVSG | ADAVIKLTGL VTLTTSAFAT |
| 1021 EVLTLA | | | | |

In this specification, the word "protease" with reference to *Caulobacter* means the native protease disclosed in this specification which cleaves hybrid S-layer protein monomers. This protease exhibits sequence similarity to *Caulobacter* S-layer protein monomer and presence of the protease may be detected by determining whether a modified S-layer monomer produced by a *Caulobacter* exhibits the "proteolytic phenotype" described herein. Absence of the protease (or absence of the protease activity) may be similarly determined by absence of or loss of the proteolytic phenotype.

In this specification, the terms "isolated" or "isolate" with reference to a microorganism refers to a naturally occurring or recombinant microorganism substantially free of microorganisms of another genotype or phenotype. As such, the term includes, but is not limited to a microorganism purified from a natural source.

In this specification, the term "peptide" refers to a peptide of two or more amino acids and thus, the term is used interchangeably with the terms "polypeptide" and "protein". The terms "heterologous peptide" and "passenger peptide" as used throughout this specification with reference to an S-layer protein monomer or gene refers to a sequence of amino acids or a nucleic acid encoding such a sequence of amino acids not found in S-layer protein monomer.

Throughout this specification, the term "restriction site" means a nucleic acid sequence that is recognized by a nuclease whereby the nuclease cleaves a nucleic acid in which the restriction site is located.

In this specification, the terms "library" and "panel" mean a collection or plurality of similar microorganisms, nucleic acids, or peptides with individual members (or groups of members) of the panel or library comprising a feature that is unique to that member or group of members. An example would be a collection of nucleic acids, each one of which comprises a portion encoding a detectable peptide signal with individual members or groups of members in the collection comprising nucleic acid sequences that encode unique peptides. Another example is a collection of recombinant *Caulobacter*, each of which is capable of expression of a recombinant S-layer protein monomer with the S-layer protein monomer expressed by individual members or groups of members in the collection comprising different peptides heterologous to S-layer protein monomer.

In this specification, the word "modified" with respect to a *Caulobacter* S-layer monomer refers to a non-wild type S-layer protein monomer. Such a modified monomer may contain deletions, additions, or substitutions as compared to a wild-type monomer. A modified monomer includes one differing in sequence from a wild-type monomer by as few as one amino acid as a result of the introduction of a restriction site into a gene encoding the monomer. The term "hybrid" as applied to *Caulobacter* S-layer protein monomers refers to a modified S-layer monomer comprising one or more peptides heterologous to *Caulobacter* S-layer monomers. The term "full-length hybrid" with respect to modified S-layer monomer has the meaning as set out above with respect to the background art.

In this specification, the term "native" refers to a microorganism that is in the form by which it naturally occurs, or with reference to a product of a microorganism, refers to a product that naturally occurs in a microorganism.

In this specification, the word "conservative" with respect to an amino acid substitution refers to the substitution of one amino acid for another at a given location in the peptide, where the substitution can be made without any appreciable loss or gain of function, to obtain a biologically equivalent polypeptide. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Conserved amino acid substitutions may be made where an amino acid residue is substituted for another having a similar hydrophilicity value (e.g. within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (-1.8); Tyr (−2.3); Phe (−2.5); and Trp (−3.4). Conserved amino acid substitutions may also be made where an amino acid residue is substituted for another having a similar hydrophobic index (e.g., within a value of plus or minus 2.0). In such embodiments, each amino acid residue may be assigned a hydrophobic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Conserved amino acid substitutions may also be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Protease-negative strains of *Caulobacter* according to this invention may be obtained by mutating *Caulobacter* using known methodologies, including those described herein, and selecting mutated bacteria which do not express the protease or in which the protease is not active. Activity of the protease may be readily determined using the methodologies described herein. It may also be possible to identify and isolate naturally occurring strains of *Caulobacter* which may not produce the protease, for example by screening different strains of the bacteria for presence of the metalloprotease activity or for presence of polynucleotides homologous to the *Caulobacter* native polynucleotides encoding the protease.

Protease-negative *Caulobacter* of this invention may now be obtained through mutation of *Caulobacter* by making use of the information herein pertaining to the nucleic acid sequence of sap (Table 2; SEQ ID NO: 2) or the amino acid sequence of Sap (Table 3; SEQ ID NO: 3). This sequence information may be employed to construct a plasmid comprising a mutant sap for homologous recombination with native sap in a selected *Caulobacter* to cause the native gene to be disrupted. The suicide vectors disclosed herein may be used in the construction of such a plasmid. Alternatively, known methods for site-directed mutagenesis or for introduction of a gene encoding a sap antisense sequence may be employed to produce a protease-negative *Caulobacter*.

TABLE 2

*Caulobacter* genome sequence containing sap (SEQ ID NO: 2; Genbank Accession No. AY064211). The gene is at nt 186–2326 with the –35 signal at nt 186–191, the Shine-Delgarno ribosomal binding site at nt 247–252 and the coding sequence at nt 258–2234.

```
   1 catttgaaaa ccctttttct acgaaagtcg cggacccgac atcttgcctg ggacctgcag
  61 cacaaacgcg ccatgcgagc atttagctgt ggcgcctggg caacaaagtg agttggaagc
 121 tgaaaaaggt gacgaaggcc accccgccaa ggtctggctc cgcccgagcg agcgctgtgc
 181 gaacttgtcg caaatagcca agattgcaga agaaattctg cttctccata ctcctttcag
 241 gtgagtggag cgcgtcggtg tgtagtcagt gcgagcggta tggactgaac ctccacgggg
 301 atgatgtcgc cccggccgtc tcgggtggcg agggtcccta cgcgtttgtc gacgccgact
 361 tgctgcgcag cgagccgggc tggtcgaacc agttcctggt ccccgcgacc gtgacctatg
 481 cgttccgcgc gaccgcaccg gcgagcatgc ccagcgatac gggcggcttt tcgcagttca
 541 acgccgccca gatcctccag gccgagaagg cgctgcaggc ctggtccgac gtcgccaaca
 601 tcacctttgt ccgcgtgggc cagggcacgt cgggcgaggc cgcctacagc gacaacgcct
 661 cgatcctgtt cgccaatttc agcaccggca gcgagggctc ggcgggcttc gcctactatc
 721 cgggcaaccc tgcggccagc agccggtccg gcgatgtctg gatcaagtcg acggccggct
 781 acaacaccaa cccgaccggc tccaactatg gcggcatggt gctggttcac gagctggggc
 841 acgccatcgg catcgcccac cccagcgagt acaacgccag cgccgacgac accctgacct
 901 atgcggtcaa cgcgacctac taccaggaca gccgccagta cacggtaatg tcctatttca
 961 gcgaggccaa caccggcggc tcgttcggcg gcgcctacgc ctcctcgccc ctgctcgatg
1021 acatcgccgc cgcccagttg gcctatggcg ccaacatgac cacgcgcacc ggcgacacgg
1082 tgtacggctt caactcgacc gccggccgcg agtggttcgc ggcgacctcg tcctcgaccc
1141 ggctggtgtt cgcggtctgg gacgccgcg cgtcgacac cctggacttc tccggctatc
1201 gcgtggccca gaccatcgac ctgcgagcag gctatttctc cagcgtcggc ggcctgaagg
1261 gcaatgtcac catcgccatg aacgcggtga tcgagaacgc catcggcggc tcggcggccg
1321 acaccatcaa cggaaacgct gtcgacaacc ggctgaccgg cggcgcgggc gccgacatcc
1381 tggacggcgg ccggggcgtc gacaccgccg tcttctccgg cgcctacggc aactacaccc
1441 tgaccgccgc cacgaacggc gcctggtcgg tgctcgaccg ggtggggacg gacgccaccg
1501 atacctggc gaacatcgag ttcctggcct ttaccgatcg gaccgtgacg ctcgtcgaca
1561 gccgcgtcgc gaccgcgatc agcaatatcc tgcgcctgca gaccttcagc gcctcggccg
1621 aaccgctgtc caagagcctg gcggcctcga tggccgccgg cgccagccat agcgacgcca
1681 tcggccaggt gtccaagacc gcgctgtcga ccagcggggt ggcggtgctg gcctatcagt
1741 tcttcaccgg caagacgccc acggcggccg gcatggatta tctggtcaat ccggacggcg
1801 tgaacgccaa caacctcaac agcgcctact atcagtcgtt caatctcgag aaccgctaca
1861 tcaacttcgc ggtcaatctg ggcaagatcg gcgagggagc caccaagttc ctggccgact
1921 atggcgggct cagcctgttt gacgccacgc gcaaggccta tgcgaccatc tttggcctga
1981 cgcccaccga cgacaaggtg cgcgccctga tcgacggccg caccgactac ttcgccgcct
2041 atggccagga cgggccaaac ggccaggaa ccaaggcggc catggtgggc tggctgatgg
2101 ccgaggcggg caaggccgac atcggcgtct acgccaagtc ggcggggcc ttcttcgccg
2161 accaggccac caagaatgtc tatggcgtgg atctgatcgg cgtctacgcc aagccggaat
```

TABLE 2-continued

*Caulobacter* genome sequence containing sap (SEQ ID NO: 2; Genbank Accession No. AY064211). The gene is at nt 186–2326 with the -35 signal at nt 186–191, the Shine-Delgarno ribosomal binding site at nt 247–252 and the coding sequence at nt 258–2234.

```
2221 acaacctcat ctgaccgttc gaagggcgcg gcgacaaagg tccagacagc gatttgaagg 2281 gagtaagggc gggcggccct cccccgaaaa ggtcgccgcc cgagttgctt
```

TABLE 3

Sap amino acid sequence (SEQ ID NO: 3; GenBank accession no. AAL47190) in which underlining indicates a metalloprotein active-site having consensus sequence HEXXHXUGUXH (SEQ ID NO: 4) in which X represents an arbitrary amino acid and U is a bulky hydrophobic residue (Baumann, et al. 1993). The sequences double-underlined indicate $Ca^{+2}$ binding sites having consensus sequence GGXGXD (SEQ ID NO: 5) where X is an arbitrary residue (Baumann, et al. 1993).

```
  1 MCSQCERYGL NLHGDDVAPA VSGGEGPYAF VDADSRVGTV DGKKSLTVPE AALQLLRSEP

61 GWSNQFLVPA TVTYAFRATA PASMPSDTGG FSQFNAAQIL QAEKALQAWS DVANITFVRV

121 GQGTSGEAAY SDNASILFAN FSTGSEGSAG FAYYPGNPAA SSRSGDVWIK STAGYNTNPT

181 GSNYGGMVLV HELGHAIGIA HPSEYNASAD DTLTYAVNAT YYQDSRQYTV MSYFSEANTG

241 GSFGGAYASS PLLDDIAAAQ LAYGANMTTR TGDTVYGFNS TAGREWFAAT SSSTRLVFAV

301 WDAGGVDTLD FSGYRVAQTI DLRAGYFSSV GGLKGNVTIA MNAVIENAIG GSAADTINGN

361 AVDNRLTGGA GADILDGGRG VDTAVFSGAY GNYTLTAATN GAWSVLDRVG TDATDTLANI

421 EFLAFTDRTV TLVDSRVATA ISNILRLQTF SASAEPLSKS LAASMAAGAS HSDAIGQVSK

481 TALSTSGVAV LAYQFFTGKT PTAAGMDYLV NPDGVNANNL NSAYYQSFNL ENRYINFAVN

541 LGKIGEGATK FLADYGGLSL FDATRKAYAT IFGLTPTDDK VRALIDGRTD YFAAYGQDGP

601 NGQGTKAAMV GWLMAEAGKA DIGVYAKSAG AFFADQATKN VYGVDLIGVY AKPEYNLI
```

Protease-negative *Caulobacter* strains of this invention may be used according to known methodologies to express heterologous peptides within an S-layer protein monomer or as a C-terminal hybrid protein in which a heterologous peptide is attached to a C-terminal secretion signal of the S-layer protein. In this way, unwanted cleavage of the modified or hybrid S-layer gene product is minimized.

Protease-negative *Caulobacter* for use as an expression system according to this invention will comprise at least a *Caulobacter* S-layer protein C-terminal secretion signal operably linked to a promoter capable of expression in *Caulobacter*. This DNA construct may also comprise DNA encoding sufficient N-terminal part of *Caulobacter* S-layer protein or monomer to provide for adherence of the S-layer protein to the cell surface, once the protein is secreted from the cell. The construct may comprise DNA encoding substantially all of a *Caulobacter* S-layer protein or protein monomer in which the coding sequence is interrupted by insertion of heterologous DNA. In any case, the heterologous DNA in the construct may be one or more restriction sites to facilitate insertion of further heterologous DNA and/or the heterologous DNA may comprise DNA encoding a peptide, polypeptide, or protein heterologous to *Caulobacter* S-layer protein.

Extensive information is available for making *Caulobacter*/S-layer expression systems intended to express full-length hybrid proteins which are displayed on the cell surface (Bingle, et al. [1997(b)]; and, Umelo-Njaka, E., et al. [2000]), including selection of suitable *Caulobacter* hosts and construction of plasmids suitable for replication in both *E. coli* and *Caulobacter* which may be used for expression of hybrid S-layer protein monomers from the host *Caulobacter*. Preferred *Caulobacter* hosts do not have a functional native S-layer protein monomer gene and instead express only S-layer protein monomer as directed by recombinant DNA that is either plasmid borne or integrated into the bacterial genome.

Preferred sites for insertion of heterologous DNA sequences into S-layer encoding DNA to produce full-length hybrid proteins have been previously published and may also be determined according to methodologies known in the art. Use of protease-negative strains may make available additional sites since the coding product is not subject to degradation by the metalloprotease.

*Caulobacter* is particularly suited for display of foreign peptides in view of the wide variety of peptides that may be expressed as part of the S-layer protein and the high copy number of foreign peptide that can be displayed per unit area of the bacterial surface. Successful insertions may be displayed at a number as high as about 20,000-40,000 copies per cell. This allows for very high sensitivity and screening and the ability to look for affinity binding interactions. In comparison, conventional phage display is often limited to one copy number per phage particle, particularly with peptides over about 10-15 amino acids in length. Also, since *Caulobacter* are capable of forming spontaneous, monolayer biofilms, for certain applications in the area of peptide/protein library screening, the ability to readily attach bacterial cells to a surface at high density will be useful. This facilitates handling of a library of modified cells and for controlling exposure of test compounds to the modified cells.

Preparation of Presentation Libraries Using *Caulobacter*

In this method, a plasmid containing all or sufficient part of an S-layer protein monomer gene to provide for secretion and adherence of the S-layer monomer is employed. Preferably, the plasmid will contain substantially all of the S-layer coding region and at least one pair of restriction sites to be used for direct oriented cloning of DNA fragments into the S-layer gene. Preferably, these sites will be located at a preferred position in the S-layer coding region demonstrated to be a permissible site for insertion of heterologous material. This can be determined according to preferred sites described in the art or by positioning other peptides at that site and determining whether the peptide is available for antibody binding and does not disrupt secretion, assembly, and attachment of the S-layer array. For example, unique BamH1 restriction sites may be installed by linker mutagenesis as described in PCT patent application published under WO 97/34000. At these sites, one may then install a short set of oligonucleotides which would modify the sites to contain other restriction sites, for example a NcoI and a PstI site in a selector order. The plasmid vector is preferably one that replicates both in *Caulobacter* as well as another system such as *E. coli* to facilitate amplification of clones showing a positive result when presented to a target compound. A suitable plasmid may be those previously described which contain a promoter recognized by *Caulobacter* and into which the S-layer gene may be placed. For example, such a vector is pWB9 as described by Bingle, et al. (1997a). Preferably, the *Caulobacter* employed for presentation of the library will be a protease-negative strain as described herein.

To produce a library, oligonucleotides may be synthesized to contain known sequences flanking a variable sequence. The known sequences may be required for proper digestion or ligation at restriction sites and for hybridization to primers for polymerase extension reactions. The middle region of the oligonucleotide may be prepared by instructing a DNA synthesizer to vary all four bases at each position. After synthesis, an oligonucleotide complementary to one end may be added and using a polymerase reaction, a double-stranded version provided. The double-stranded DNA may be digested with appropriate restriction enzymes (e.g. NcoI and PstI) making the oligonucleotides ready to be cloned into the corresponding receptor sites of the S-layer gene on the plasmid. This may be done by a ligation reaction and the plasmids then electroported en masse into *Caulobacter* cells using previously described techniques. All resulting colonies may be pooled and stored in a freezer until required for screening.

An advantage in using protease-negative host *Caulobacter* is in preparation and screening of large libraries of inserts into the S-layer. These could result from construction of combinatorial peptide libraries (achieved via random or semi-random synthesis of oligonucleotides [and subsequent cloning into the S-layer] that specify peptides, usually of a fixed length of 8-12 amino acids) or for the cloning of random fragments of bacterial genomes or cDNA figments. In such cases minimizing the number of clones that are lost or poorly represented because of cleavage of the insert is important to ensure the maximum probability that clones of utility are contained in the library.

It is typical in the use of such libraries that one is searching for very rare events—those which bind a ligand of interest. If one is searching for vaccine candidates from a genome fragment library the ligand could be an antibody present in sera from patients recovered from an infection. A typical example of an application of combinatorial peptide libraries would be to find peptides that bind to components of a signal transduction cascade to understand the specific interactions that occur. In other cases one may be searching for a peptide sequence that would bind to a molecule of therapeutic value. Thus one could use the peptide as a key component of an affinity matrix that would be used to purify the therapeutic molecule.

Another advantage of S-layer display is that the displaying bacterium is large enough to be readily detected by automated cell sorting methods, including fluorescence-activated cell sorting (FACS). An apparatus for performing FACS is referred to as a "flow cytometer". In practice one derivatizes a target molecule of interest (i.e. the one for which one expects to find binding peptides in the library) with a fluorescent tag (e.g., fluorescein). One then uses a FACS apparatus to find and segregate the rare library members that bind to the fluorescent tag.

One method of doing so is to use a Bectin-Dickinson FACS machine (model BD FACS Vantage™ TSO SE), equipped with a 50 μm nozzle, using 26 psi of pressure to create a sample stream. The stream is broken into droplets using 40,000 Hz generator. The sample threshold triggered on Fl-1(530/40 nm filter) to exclude non-fluorescent bacteria. This apparatus is able to detect the specific fluorescence of fluorescein and deflect cells displaying a sufficient amount of that label into a collection device thereby segregating the cells. This collection device may be a single tube, to pool all "hits". The apparatus is also capable of allowing individual cells ("hits") to be directed to individual wells of a standard 96 well microtiter plate. These wells would contain culture medium, enabling outgrowth of the individual sorted cells for long-term storage and later experiments.

FACS methodology to identify clones in *Caulobacter* operates much faster than the prevalent alternative technologies such as library display of peptides on bacteriophage. It is practical to consider examination of a *Caulobacter* library by the above methods in 1-2 hours. After FACS is performed, one would grow a quantity of the cells that have been diverted as "hits" by adding culture medium. Samples of the cultured cells may be lysed and the plasmid DNA subjected to DNA sequencing. An oligonucleotide known to hybridize to the flanking region of the variable sequence may be employed with a polymerase in a thermocycler apparatus to amplify the region of interest to facilitate sequence determination. The sequence of individual clones will be read and evaluated. Desired clones may be retrieved from replicate samples.

EXAMPLES

Bacterial Strains and Plasmids

Bacterial strains and plasmids are listed in Tables 4 and 5. *Escherichia coli* strains were grown at 37° C. in Luria-Bertani (LB) medium. When required, antibiotics were included in LB medium at the following concentrations: streptomycin (Sm), 50 μg/ml, kanamycin (Km), 50 μg/ml, ampicillin (Ap), 50 µg/ml, gentamycin 30 µg/ml and chloramphenicol (Cm), 20 µg/ml.

*C. crescentus* was grown at 30° C. peptone-yeast extract (PYE) medium (0.2% peptone, 0.1% yeast extract, 0.01% CaCl$_2$, 0.02% MgSO$_4$, 1.2% agar). When required, antibiotics were included in PYE medium at the following concentrations: streptomycin (Sm), 50 µg/ml, kanamycin (Km), 50 µg/ml, and chloramphenicol (Cm) 2 µg/ml.

Solidified LB and PYE medium was prepared by adding agar to a final concentration of 1.2% w/v.

TABLE 4

Bacterial Strains

| Strain | Relevant Characteristics | Source/Reference |
|---|---|---|
| *Escherichia coli* | | |
| DH5α | recA$^-$, endA$^-$ | Life Technologies |
| | | Burlington, ON |
| | | Canada |
| S-17 λ pir | recA$^-$, Sm$^R$, Km$^R$ carries λ pir prophage | De Lorenzo, et al. (1993) |
| *Caulobacter* | | |
| JS4000 | RsaA$^-$ mutant of *C. crescentus* strain CB2 (ATCC 15252) | Smit and Agabian (1984) |
| JS4020 | Strain JS4000 with plasmid pTZ18U; rsaAΔP (485/IHNVG20) integrated into its chromosome | |
| JS4021 | Sap$^-$ Tn5 mutant of strain JS4000 | |
| JS4015 | Sap$^-$ UV/NTG mutant of strain JS4000 | |

TABLE 5

Plasmids

| Plasmid | Relevant Characteristics | Reference |
|---|---|---|
| pG8 | Source of IHNV-G gene, Ap. | Xu, et al. (1991) |
| pHP45Ω | Source of the HindIII fragment carrying the Sm$^R$ gene for construction of pTZ18USm | Fellay, et al. (1987) |
| pHP45Ω-Km | Source of the HindIII fragment carrying the Km$^R$ gene for construction of pBBR1MCS: kmsap | Fellay, et al. (1987) |
| pAG408 | Suicide vector for Tn5 mutagenesis; ColE1, Gm, Km, Ap. | Suarez, et al. (1997) |
| pBBR1MCS | Broad-host range cloning/expression vector; Cm. | Kovach, et al. (1994) |
| pBSK, pBSKII | Phagemid cloning/expression vectors; ColE1, Ap. | Stratagene, La Jolla CA |
| pTZ18U, pTZ19U | Phagemid versions of pUC18 and pUC19 (Yanisch-Perron, et al. 1985); gene expression driven by *E. coli* lac promoter; ColE1, Ap. | Amersham Life Sciences Mississauga, ON Canada |
| pTZ18UB | pTZ18U lacking a BamHI site; the BamHI site was destroyed by BamHI digestion, polishing with PolIK and religation: Ap. | Bingle, et al. (1997a) |
| pTZ18USm | pTZ18U with a Sm$^R$ gene inserted as a PolK polished HindIII fragment to the ScaI site of the Ap$^R$ gene; Sm. | |
| pWB9KSAC | Expression vector derived from pKT215 (Bagdarsian, et al., 1981) incorporating the rsaA promoter; Cm, Sm. | Bingle, et al. (1997a) |
| pWB9KSAC: rsaAΔP | A promoterless version of the rsaA gene (rsaAΔP) in pWBKSAC; Cm, Sm. | Bingle, et al. (1997a) |
| pUC9CXS | pUC9 (Vieira and Messing, 1982) with a modified multiple cloning site, Ap, Cm; used to provide DNA fragments with suitable BamHI termini for inframe insertion into BamHI linker mutated rsaAΔP genes. | Bingle, et al. (1997a) |
| pTZ18UB: rsaA (AciI485BamHI) | rsaAΔP carrying a BamHI linker insertion at a AciI site corresponding to amino acid 485 of RsaA in pTZ18UB; Ap. | Bingle, et al. (1997b) |

TABLE 5-continued

Plasmids

| Plasmid | Relevant Characteristics | Reference |
| --- | --- | --- |
| pTZ18UB: rsaA (MspI450 BamHI) | rsaAΔP carrying a BamHI linker insertion at a MspI site corresponding to amino acid 450 of RsaA in pTZ18UB; Ap. | Bingle, et al. (1997b) |
| pTZ18UB: rsaA (HindPII 723BamHI) | rsaAΔP carrying a BamHI linker insertion at a MspI site corresponding to amino acid 450 of RsaA in PTZ18UB; Ap. | |
| pWB9KSAC: rsaAΔP (450/Pilin12) | rsaAΔP carrying a DNA insert encoding 12 amino acids of P. aeruginosa pilin at a position corresponding to amino acid 450 of RsaA in pWB9KSAC. | Bingle, et al. (1997b) |
| pWB9KSAC: rsaAΔP (723/3XPilin12) | rsaAΔP carrying a DNA insert encoding tandem 3 copies of pilin epitope at a position corresponding to amino acid 723 of RsaA in pWB9KSAC. | |
| pWB9KSAC: rsaAΔP (723/VP2C) | rsaAΔP carrying a DNA insert encoding amino acids 145–257 of the VP2 glycoprotein of IHNV at a protein corresponding to amino acid 723 of RsaA in pWB9KSAC. | |
| pTZ18UB/pWBK SAC: rsaAΔP (485/IHNVG20) | rsaAΔP carrying a DNA insert encoding 20 amino acids of IHNV-G at a position corresponding to amino acid 485 of RsaA in pTZ18UB or pWBSAC. | |
| pTZ18UB/pWBK SAC: rsaAΔP (450/IHNVG20) | rsaAΔP carrying a DNA insert encoding 20 amino acids of IHNV-G at a position corresponding to amino acid 450 of RsaA in pTZ18UB or pWBSAC. | |
| pTZ18Usm: rsaAΔP (485/IHNVG20) | rsaAΔP carrying a DNA insert encoding 20 amino acids of IHNV-G at a position corresponding to amino acid 485 of RsaA in pTZ18Usm. | |
| pBBR1MCS: Kmsap | pBBR1MCS with 2 fragments inserted into its multiple cloning site (MCS): (1) a 2.2-kb HindIII/BamHI fragment carrying the sap gene and (2) a 1.5-kb HindIII fragment carrying a $Km^R$ gene. The orientation of fragment (1) allows expression of the sap gene from either its native promoter or the lac promoter of pBBR1MCS; Cm, Km. | |
| pBBR1MCS: sap | Equivalent to pBBR1MCS: Kmsap without the 1.5-kb fragment (2). | |

Recombinant DNA Methods

Chromosomal DNA was isolated from *Caulobacter* using standard methods (Sambrook, et al., 1989), while plasmid DNA was isolated from *E. coli* and or *Caulobacter* using the boiling method (RSF1010-based plasmids; Holmes and Quigley, 1981) or the alkaline lysis method (all other plasmids; Birnboim and Doly, 1979). Plasmid DNA was introduced into *E. coli* and *Caulobacter* by electroporation as described by Gilchrist and Smit (1991).

DNA-modifying enzymes were purchased from Life Technologies (Burlington, ON, Canada) or New England Biolabs (Mississauga, ON, Canada) and were used according the manufacturer's instructions.

Agarose gel electrophoresis (Tris-Borate-EDTA buffer) was conducted by standard methods (Sambrook, et al., 1989); in preparative applications, DNA fragments were purified using QIAEX II (Qiagen Inc., Chatsworth, Calif.).

Southern hybridization was done using standard methodologies (Sambrook, et al., 1989; and, Taso, et al., 1983). DNA samples were electrophoresed on a 0.8% agarose gels and probed with oligonucleotides labeled with {α-32P} dCTP (Amersham) using the Rediprime II™ random prime labeling system (Amersham Pharmacia Biotech, UK).

Polymerase chain reaction (PCR) amplification was conducted by using TaqI or Pfx DNA polymerase (Life Technologies, Burlington, ON, Canada) according to manufacturer's instructions and a Techne Progene™ Thermal Cycler (Mandel Scientific Co., Guelph, ON, Canada).

Nucleotide sequencing was performed on an ABI PRISMTM™ 377 automated sequencer. Oligonucleotides were synthesized using a Perkin-Elmer ABI synthesizer.

Isolation of RsaA

Wild-type S-Jayer protein (RsaA) and full-length RsaA hybrid proteins were isolated from *Caulobacter* cells by low-pH extraction (Walker, et al. 1992; and, Nomellini, et al. 1997). Mid log phase cells ($OD_{600}$ of 0.5 to 1.0) were washed once in 10 mM HEPES buffer, pH=7.2 by centrifugation (10,000×g, 5 min) and then resuspended by vortexing in 100 mM HEPES buffer, pH 2.0 equivalent to 5% of the original culture volume. After 5 min at room temperature, the cells were pelleted by centrifugation and the supernatant fluid containing RsaA was recovered.

SDS-PAGE and Western Analysis

SDS-PAGE was conducted by the discontinuous gel method of Laemmli (1970); samples were treated at 37° C., rather than boiling, in SDS-PAGE sample buffer prior to electrophoresis (Smit and Agabian, 1984). Western immunoblot analysis was carried out as described by Walker, et al. (1994) using an anti-RsaA polyclonal antibody as a probe. Antibody binding was visualized using goat anti-rabbit or mouse serum coupled to horse-radish peroxidase and colour-forming reagents. Before analysis of low-pH extracted RsaA by SDS-PAGE, 2 µL of 1 N NaOH was added per 20 µL of extracted protein.

Western colony immunoblotting (Bingle, et al. 1997b) was performed by spread plating cells on PYE agar to a density of approximately 100-200 cfu's per standard Petri plate. Following incubation for 3-4 days at 30° C., nitrocellulose membranes were pressed onto surface of the plates for 2 min. The membranes with adherent colonial material were then lifted-off, allowed to air dry for 5-10 min, blocked with 5% skim milk and finally processed as above.

Amino Terminal Sequence Determination

Protein samples for N-terminal sequencing were electrophoretically transferred from SDS-PAGE gels to a 0.2 µm PVDF membrane (Bio Rad) using a BioRad transfer apparatus according to the manufacturer's instructions. The membrane was briefly stained in Coomassie blue R-250 (Sigma) destained in 50% methanol and air dried. The desired protein band was excised from the membrane using a scalpel and the N-terminal amino acid sequence was obtained by automated Edman degradation.

Construction of Strain JS4020

A sample of plasmid pTZ18USm:rsaAΔP(485/IHNVG20) was electroportated into the Sm sensitive, RsaA⁻ strain: JS4000. The resulting cell suspension was plated on solid PYE medium containing 50 µg/mL of Sm to select for cells containing the chromosomally integrated plasmid resulting from a single cross-over event between the plasmid borne copy of rsaA and the chromosomal copy of rsaA in strain JS4000. Sm resistant (SM$^R$) cells from several colonies were then screened by low-pH extraction for the presence of cell-surface bound S-layer protein fragments characteristic of proteolytic cleavage within the IHNV-G insert as well as proteolytic cleavage within the RsaA N-terminus (the "proteolytic phenotype"; see FIG. 1). One isolate exhibiting both Sm-resistance and the expected proteolytic pattern was retained and designated stain JS4020.

Tn5 Mutagenesis of JS4020

Conjugation was used to introduce a Tn5 derivative carried by the suicide vector pAG408 into JS4020. 100 µL of an overnight culture of E. coli S-17 λ pir (pAG408) was mixed with 1 mL of an early log phase culture of JS4020 in 5 mL of 10 mM MgSO$_4$. The cell mixture was collected on a sterile 22 mm diameter nitrocellulose filter paper and the filter paper was placed on the surface of PYE agar in a petri dish. After overnight incubation at 30° C., the cells were dislodged from the filter in 5 mL of 10 mM MgSO$_4$ and 100 µL aliquots were plated on PYE agar containing 50 µg/mL each of Km and Sm.

UV/NTG Mutagenesis of JS4000

A mutant pool of strain JS4000 previously created by ultraviolet (UV) light mutagenesis (Ong, C., et al. [1990] was further mutagenized using nitrosoguanidine (NTG) according to the method of Miller (1972).

Characterization of Caulobacter Protease

As reported in Bingle, et al. (1997b), insertion of a 12 amino acid peptide derived from aeruginosa pilin at centrally-located positions in the full-length 1026 amino acid RsaA primary sequence often results in cleavage of the hybrid protein within the pilin-peptide insert and/or at a site distant from the insertion site within the N-terminus of RsaA. Cleavage within the pilin peptide insert yields 2 fragments which remain bound to the cell surface while cleavage within the RsaA N-terminus yields a 26 kDa N-terminal cleavage product which remains surface-bound, and a C-terminal fragment which is released into the growth medium (FIG. 1). For the purposes of this specification, cells exhibiting the proteolytic phenomena shown in FIG. 1 are said to possess the "proteolytic phenotype".

Using conventional techniques, we determined that Caulobacter exhibits a protease activity that is not energy dependent (ATP does not stimulate the activity); the protease activity occurs free inside the cell and is not associated with cell membranes or the periplasm of this Gram negative organism; EDTA is somewhat inhibitory (a characteristic of metalloproteases); there is no induction of the enzyme stimulated by the presence of a recombinant S-layer protein shown to be cleaved; and, there is an absence of other cell proteins being affected by the protease, when it is degrading a recombinant S-layer protein. Insertions which result in consistent cleavage of a recombinant product tend to be in the central ⅔ of the S-layer coding region, with sites near the N or C-terminal regions tending to be safe from protease effects. This information, coupled with the sequence information described below indicates that the protease attaches to the monomer and has a limited range along the length of the protein to act upon. The C-terminal region is needed as a secretion signal for the S-layer protein, and the N-terminal region is needed for attachment of the S-layer protein assembly to the cell surface.

C. crescentus (strain CB2A) was treated with ultraviolet light or chemical mutagens as described above, at rates permitting about 1% cell survival. Individual cells surviving the mutagenesis received a plasmid version of the S-layer gene containing a heterologous insertion shown to be efficiently cleaved according to the proteolytic phenotype. Colonies were then screened using an immunoblot method involving overlaying the colony with a nitrocellulose disk followed by removal of the disk and treatment with S-layer protein-specific antibodies in a manner essentially the same as used in Western-Blot method. A typical result is a "halo" of antibody reactivity surrounding the colony, due to the cleavage of the monomer which then prevents it from assembling into a crystallized, surface-attached S-layer. Colonies that fail to produce a halo are rare and these were selected for subsequent confirmation that they lacked the ability to cleave the recombinant S-layer molecule in the manner seen by wild-type cells.

Characterization of Proteolysis of IHNV-G Peptide Inserts

In order to confirm that the proteolytic phenotype is not associated with just pilin peptide inserts, a 20 amino acid vaccine epitope (ASESREELLEAHAEIISTNS; SEQ ID NO: 6) derived from amino acids 306 to 325 of the infectious hematopoietic necrosis virus glycoprotein (IHNV-G) was inserted at 2 permissive sites corresponding to amino acids 485 and 450 in RsaA. The IHNV-G DNA insert was synthesized by PCR, inserted into rsaAΔP and introduced into the RsaA⁻ strain: JS4000, using the Caulobacter expression plasmid pWB9KSCAC by methodology identical to that described for pilin peptide DNA in Bingle, et al (1997a).

Despite the difference in the nature of the insert, RsaA hybrid proteins carrying INHV-G peptide insertions (100 kDa) exhibited the same proteolytic phenotype (FIG. 1) as cells synthesizing RsaA molecules carrying pilin peptide inserts. Insertion of the 20 amino acid IHNV-G peptide at either amino acid 485 or 450, resulted in the cleavage of the hybrid protein within the peptide insert yielding 250 kDa fragments, consistent with cleavage within the IHNV-G insert (FIG. 4A), as well as the surface-bound 26 kDa fragment. Native RsaA (98 kDa) was not subjected to cleavage (FIG. 4A).

N-terminal microsequencing revealed that the cleavage of INHV-G insert occurred between an Arg and Ser residue. This cleavage site was not located within the IHNV-G peptide itself but rather in the portion encoded by the 3' fusion joint between IHNV-G DNA and rsaA DNA, as was the case for pilin peptide insertions.

Tn5 Mutagenesis of JS4020

When proteolytic cleavage of a RsaA hybrid protein occurs at an N-terminal site distant from the site of the heterologous insertion, the C-terminal cleavage product fragment is shed from the cell surface. In colony immunoblots probed with RsaA antibody, this shed RsaA fragment yields an immunoreactive halo around colonies. Tn5 mutagenesis leading to the loss of the proteolytic phenotype may be detected by screening for loss of this halo around colonies using colony immunoblot technique.

Strain JS4020 was used as a background to detect the loss of the proteolytic phenotype as the result of Tn5 mutagenesis. This strain possesses a chromosomal copy of rsaA carrying a DNA insert encoding the 20 amino IHNV-G peptide at a site corresponding to RsaA amino acid 485.

Tn5 mutagenesis of strain JS4020 was conducted as described above and the resulting mutants were subjected to colony immunoblot assays. To confirm the loss of the proteolytic phenotype and to screen out Tn5 insertions in rsaA or components of its secretion apparatus, cells from colonies showing halo loss were further screened for the presence of the undegraded RsaA/IHNVG hybrid protein using the low-pH extraction method coupled with SDS-PAGE.

Isolation of Tn5 Interrupted Chromosomal DNA

Three mutants of JS4020 clearly exhibiting loss of the proteolytic phenotype were isolated. Chromosomal DNA was prepared from all three mutants, digested with BamHI and BglII and subjected to Southern analysis using the 1.5 kb KpnI (Tn5) fragment from pAG408 used as a probe. Because the Tn5 derivative in pAG408 possesses single BamHI and BglII sites which occur at opposite ends of the Tn5, single DNA fragments will result from digestion of the Tn5 interrupted chromosomal DNA with either BamHI or BglII separately but together the two fragments would include the 5' and 3' portion of the interrupted region in addition to Tn5.

Relevant BglII and BamHI Tn5-tagged fragments (from digests of chromosomal DNA of all 3 mutants) were recovered from agarose gels for propagation in the BamHI site of pBSK(−). For one of the mutants, a 6 kb BamHI fragment and a 7 kb BglII fragment were successfully cloned yielding plasmids pEU1 and pEU2 respectively. The transposable region of pAG408 is 2.2 kb in length. Thus, about 4 kb and 5 kb of DNA flanking Tn5 was made available for nucleotide sequence analysis. Using the appropriate known restriction sites from pAG408 as a guide in conjunction with restriction mapping, DNA immediately flanking the Tn5 was excised from pEU1 and pEU2 and inserted into pTZ19U, yielding plasmids pTZ19UP1 and pTZ19UP7 (FIG. 2) which were sequenced.

Nucleotide Sequencing of DNA Flanking the Tn5 Insertion Site

Nucleotide sequence information from pTZ19UP1 and pTZ19UP7 concerning the DNA immediately flanking the Tn5 insertion site was used to search the nucleotide sequence of the genome of *C. crescentus* strain CB15 in the Institute for Genomic Research (TIGR) database (Nierman, et al. 2001). As a result, an open-reading frame of 1977bp initiating with GTG (gene CC0746, GenBank accession no. AE005750) was identified, which when translated, provides an N-terminal region which exhibits significant sequence similarity to several metalloproteases: most notably the alkaline protease of *Pseudomonas aeruginosa* (Okuda, K., et al. [1990]).

Although the nucleotide sequence contained in the TIGR database was derived from analysis of the *C. crescentus* genome and this example concerns JS4000 derived from strain CB2, the open reading frames initially compared between the two strains shows that the two putative protease genes (collectively termed “sap” herein) are almost identical at the nucleotide sequence level and that the TIGR sequence can be used as a guide for sequencing of the DNA flanking the Tn5 insertion site. In addition, this sequence comparison revealed both the probable orientation of the Tn5 insertion and that the insertion site was located almost exactly in the centre of the gene with approximately 1000 bp on either side of the insertion site (FIG. 3).

Using this information and the TIGR sequence as a guide to the location of suitable restriction sites, one additional pTZ19U-based plasmid, pTZ19UP4, was constructed (FIGS. 2 and 3). Using each of pTZ19U 1, 4 and 7, the nucleotide sequence encompassing 1000 bp on either side of the Tn5 insertion mutation associated with loss of the proteolytic phenotype was assembled. The sap DNA sequence and Sap amino acid sequence so derived are shown in Tables 2 and 3 above.

Analysis of Sap Sequence

The nucleotide sequence of the JS4000 sap gene (Table 2) differed by only 2 base pairs from that reported by Nierman, et al. (2001) for strain CB15. Both predict a primary translation product of 658 amino acid residues, but sequence for the JS4000 gene indicates a valine at position 217 (Table 3) while the nucleotide sequence of the reported CB15 sap gene predicts a conservative substitute (alanine) at this position. Thus, the sap gene and Sap protein for these strains are interchangeable. The congruence between the sap nucleotide sequences of strains JS4000 and CB15 extended both upstream into a putative gene encoding an OmpA-like protein and downstream into a GC-rich region with the potential to code for a stem-loop structure. These regions of DNA exhibited 100% nucleotide sequence identity between the two strains. A -35 transcription initiation signal (5'-TTGTCG-3') and a translation initiation signal (5'-GGAG-3") characteristic of *C. crescentus* housekeeping genes (Malakooti, J., et al. [1995]) were also identified in these regions of both strains.

The amino acid sequence of Sap can be divided into two regions, each of which show significant similarity to other proteins in the National Center for Biotechnology (NCBI) protein database as identified using the BLAST algorithm in conjunction with the default parameters.

The N-terminal region of Sap exhibits significant similarity to the alkaline metalloprotease (AprA) of *P. aeruginosa* (and other members of this family of proteases). Specifically, amino acids 89-417 of Sap (Table 3) have about 55% sequence identity to amino acids 92-408 of AprA. This region of the Sap protein contains the metalloprotease active site consensus sequence (HEXXHXUGUXH; SEQ ID NO: 4) as well as 4 of the 7 $Ca^{+2}$ binding consensus sequences (GGXGXD; SEQ ID NO: 5) found in AprA (also known as "RTX sequences").

The C-terminal region of Sap exhibits significant similarity to the N-terminal region of the C-terminally truncated 358 amino acid mutant S-layer protein of *C. crescentus* JS4000 as well as the N-terminal region of the wild-type S-layer proteins such as those from *C. crescentus* strains CB15 and NA1000. Specifically, amino acids 451-650 of Sap (Table 3) have about 33% sequence identity to amino acids 23-242 of RsaA (see Table 6). No other amino acid sequence in the NCBI protein database showed any significant degree of sequence similarity to the C-terminal region of Sap. Two regions of the Sap amino acid sequence show little or no similarity to sequences in the NCBI protein database: the extreme N-terminus (amino acids 1-88) and the region covering amino acids 418-540. If Sap was functionally equivalent to AprA, this region of the protein would contain a C-terminal Type I secretion signal (which is absent in Sap). The extreme N-terminal region of Sap lacks any apparent signal leader peptide and the Sap protein does not appear to contain transmembrane domains. These features indicate that Sap is localized to the cytoplasm.

was introduced into JS4015, the proteolytic phenotype was restored (FIG. 4C). The Tn5 mutation in strain JS4020 was also complemented in the same way using pBBR1MCS:sap.

Sequence analysis of PCR amplified DNA from the JS4015 sap gene indicates several scattered base changes caused by the combined NTG and UV mutagenesis. Of particular interest is a change of two adjacent bases resulting in the substitution of a Lysine residue for $Val_{188}$ of Sap, very near the protease active site.

Figure 5:
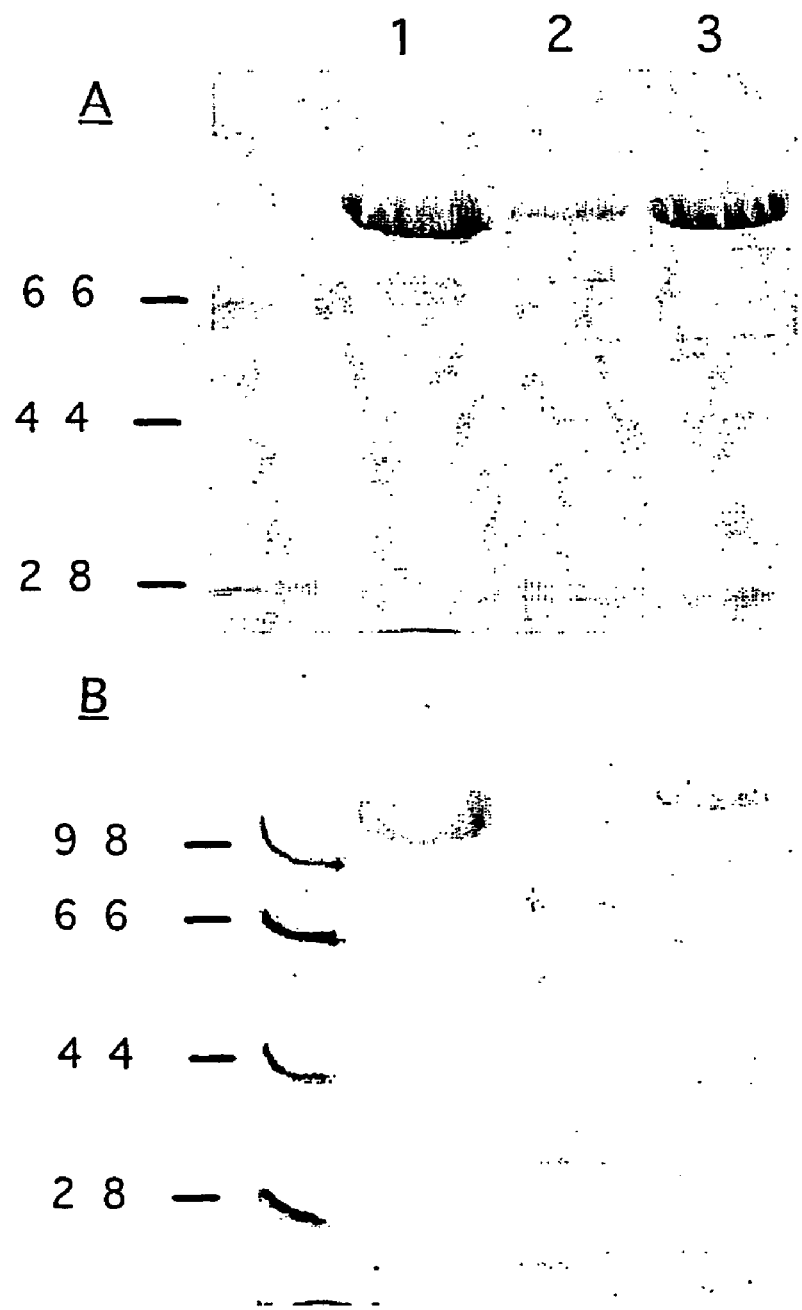
FIG. 5: a copy of a SDS-PAGE gel showing analysis of RsaA and RsaA carrying large heterologous inserts synthesized by Sap⁺ strain JS4000 and Sap⁻ strain JS4015. The proteins were extracted from the cell surface using the "low-pH" method. A. RsaA with the insertion of a 3X tandemly repeated *P. aeruginosa* pilin epitope. A 3-fold tandem repeat of the pilin tip adhesin epitope from a Type IV pilus of *P. aeruginosa* was prepared and inserted at a position in rsaA corresponding to amino acid 723 of RsaA, using methods as described in Umelo-Njaka, et al. (2000). The total length of this insertion was 134 amino acids. Lanes: 1, JS4000 (pWB9KSAC:rsaAΔP) (a no insertion control); 2, JS4000 (pWB9KSAC:rsaAΔP (723/3X Pilin12); 3, JS4015 (pWB9KSAC:rsaAΔP (723/3XPilin12). B. RsaA with the insertion of a salmonid virus glycoprotein segment. A 112 amino acid segment of the VP2 surface glycoprotein of infectious pancreatic necrosis virus (IPNV) strain SP (16) was prepared by reverse transcriptase mediated PCR, using genomic RNA derived from the virus. The segment was inserted at a position corresponding to amino acid 723 of RsaA using methods similar to those described in Bingle, et al. (1997a) and Simon, et al. (2001) for the insertion of IHNV-G amino acid sequences into RsaA. Lanes: 1, JS4000 (pWB9KSAC:rsaAΔP); 2, JS4000 (pWB9KSAC:rsaAΔP (723/VP2C); 3, JS4015 (pWB9KSAC:rsaAΔP (723/VP2C).

To ensure that the phenotype of Sap⁻ JS4015 is not simply related to IHNV-G insertions, several other full-length RsaA hybrid protein constructs known to be affected by degradation were tested. The results for two are shown in FIG. 5. In all instances significant degradation of the hybrid full-length rsaA protein occurred in a wild-type host (JS4000) while none was detected in the Sap⁻ JS4015 strain.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the invention as recited in the attached claims. All patents, patent applications, and references referred to herein are hereby incorporated by reference.

REFERENCES

Altschul, S. F., et al. (1997). Gapped BLAST and PSI-BLAST: a new generation of protein database search programs. Nucleic Acids Res. 25:3389-3402.

TABLE 6

Sequence comparison of amino acids 451–650 of Sap (SEQ ID NO: 3) to amino acids 23–242 of RsaA (SEQ ID NO: 1) with identical and similar (+) residues shown.

```
SAP451  SASAEPLSKSLAASMAAGASHSDAIGQVSKTALSTSGVAVLAYQFFTGKTPTAAGMDYLV  510
        +A+   L      +   G S + A+    K    ST+ VA+  YQFFTG  P+AAG+D+LV
RSA23   AATTLTLDAYATQTQTGGLSDAAALTNTLKLVNSTTAVAIQTYQFFTGVAPSAAGLDFLV   82

SAP511  NPDGVNANNLNSAYYQSFNLENRYINFAVNLGK-IGEGATKFLADYGGLSLFDATRKAYA  569
        +    N N+LN AYY  F  ENR+INF++NL    G GAT F A Y G+S        AY
RSA83   D-STTNTNDLNDAYYSKFAQENRFINFSINLATGAGAGATAFAAAYTGVSYAQTVATAYD  141

SAP570  TIFGLTPTD------------------DKVRALIDGRTDYFAAYGQDGPNGQGTKAAMV  610
          I G                       D + A +   T + AA   D       KAA++
RSA142  KIIGNAVATAAGVDVAAAVAFLSRQANIDYLTAFVRANTPFTAAADID----LAVKAALI  197

SAP611  GWLMAEAGKADIGVYAKSAGAFFAD-----QATKNVYGVDLIGVY                650
        G ++  A  + IG YA +  A    D      +T N  GV+L   Y
RSA198  GTILNAATVSGIGGYATATAAMINDLSDGALSTDNAAGVNLFTAY                242
```

Isolation of a Protease Deficient, Mutant in a UV/NTG Mutant Library of JS4000

In order to create a Sap− mutant lacking a Tn5 insertion, a pool of UV/NTG mutagenized JS400x was transformed with pWBKSAC:rsaA(485/IHNVG20) and screened for loss of the proteolytic phenotype (FIG. 4B). Screening of approximately 20,000 colonies resulted in the identification of 3 mutants lacking the proteolytic phenotype. One was selected and designated JS4015.

Complementation analysis was used to confirm that the UV/NTG induced mutation was located in the sap gene. JS4015 was transformed with pBBR1MCS:Kmsap (a broad host range plasmid compatible with pWBKSAC) carrying a PCR amplified copy of the sap gene from JS4000. PCR primers were chosen to amplify a sequence 140 bp upstream and downstream of the sap coding region to capture the native promoter of the sap gene. When pBBR1MCS:Kmsap Awram, P., and Smit, J. (1998). The *Caulobacter crescentus* paracrystalline S-layer protein is secreted by an ABC transporter (type I) secretion apparatus. J. Bacteriol. 180: 3062-3069.

Bagdasarian M., et al. (1981). Specific purpose plasmid cloning vectors. II. Broad-host-range, high-copy-number, RSF1010-derived vectors, and host vector system for gene cloning in *Pseudomonas*. Gene 16: 237-247.

Baumann, U., et al. (1993). Three-dimensional structure of the alkaline protease of *Pseudomonas aeruginosa*: a two domain protein with a calcium binding parallel beta roll motif. EMBO J. 12:3357-3364.

Bingle, W. H., et al. (1997a). Linker mutagenesis of the *Caulobacter crescentus* S-layer protein. Toward a definition of an N-terminal anchoring region and a C-terminal secretion signal and the potential for heterologous protein secretion. J. Bacteriol. 179: 601-611.

Bingle W. H., et al. (1997b). Cell-surface display of a *Pseudomonas aeruginosa* strain K pilin peptide within the paracrystalline S-layer of *Caulobacter crescentus*. Mol. Microbiol. 26: 277-288.

Bingle, W. H., et al. (2000). The secretion signal of the *Caulobacter crescentus* S-layer protein is located within the C-terminal 82 amino acids of the molecule. J. Bacteriol. 182: 3298-3301.

Birnboim H. C. and Doly J. (1979). A rapid alkaline extraction procedure for screening recombinant plasmid DNA. Nuc. Acids Res. 7: 1513-1523.

De Lorenzo, V., et al. (1993). Engineering of alkyl-and haloaromatic-responsive gene expression with mini-transposons containing regulated promoters of biodegradative pathways of *Pseudomonas*. Gene 130: 41-46.

Fellay, R., et al. (1987). Interposon mutagenesis of soil and water bacteria: A family of DNA fragments designed for in vitro insertional mutagenesis of Gram-negative bacteria. Gene 52:147-152.

Gilchrist, A., et al. (1992). Nucleotide sequence analysis of the gene encoding the *Caulobacter crescentus* paracrystalline surface layer protein. Can. J. Microbiol. 38: 193-202.

Gilchrist, A. and Smit, J. (1991). Transformation of freshwater and marine caulobacters by electroporation. J. Bacteriol. 173: 921-925.

Holmes, D. S. and Quigley, M. (1981). A rapid boiling method for the preparation of bacterial plasmids. Anal. Biochem. 114: 193-197.

Kovach, M. E. (1994). pBBR1MCS: a broad-host-range cloning vector. Biotechniques 16:800-802.

Laemmli, U. K. (1970). Cleavage of structural proteins during the assembly of the head of bacteriophage T4. Nature 227: 680-685.

Malakooti J., et al. (1995). A consensus promoter sequence for *Caulobacter crescentus* genes involved in biosynthetic and housekeeping functions. J. Bact. 177:4372-4376.

Miller, J. F. (1972). Experiments in molecular genetics. Cold Spring Harbor Laboratory. Cold Spring Harbor, N.Y.

Nierman, W. C., et al. (2001). Complete genome sequence of *Caulobacter crescentus*. Proc. Natl. Acad. Sci. U.S.A. 98: 4136-4141.

Nomellini, J. F., et al. (1997). Factors controlling in vitro re-crystallization of the *Caulobacter crescentus* paracrystalline S-layer. J. Bacteriol.179: 6349-6354.

Okuda, K., et al. (1990). Complete nucleotide sequence of the structural gene for alkaline proteinase from *Pseudomonas aeruginosa* IFO 3455. Infect. Immun. 58: 4083-4088.

Ong, C., et al. (1990). Attachment of the adhesive holdfast organelle to the cellular stalk of *Caulobacter crescentus*. J. Bacteriol. 172: 1448-1456.

Sambrook, J., et al. (1989). Molecular cloning, 2nd. ed. Cold Spring Harbor Laboratory, Cold Spring Harbor, N.Y.

Simon , B., et al. (2001). Recombinant vaccines against infectious hematopoietic necrosis virus: Production by the *Caulobacter crescentus* S-layer protein secretion system and evaluation in laboratory trials. Dis. Aquat. Org: 44:17-27.

Smit, J., and Agabian, N. (1984). Cloning of the major protein of the *Caulobacter crescentus* periodic surface layer: Detection and characterization of the cloned peptide by protein expression assays. J. Bacteriol. 160: 1137-1145.

Smit, J., et al. (1981). Periodic surface array in *Caulobacter crescentus*: fine structure and chemical analysis. J. Bacteriol. 146: 1135-1150.

Smit., J., et al. (1992). The S-layer of *Caulobacter crescentus*: Three-dimensional image reconstruction and structure analysis by electron microscopy. J. Bacteriol. 174: 6527-6538.

Smit, J., et al. (2000). Characterization of high density monolayers of the biofilm bacterium *Caulobacter crescentus*; evaluating prospects for developing immobilized cell bioreactors. Can. J. Microbiol. 46: 339-349.

Suarez, A., et al. (1997). Green fluorescent protein-based reporter systems for genetic analysis of bacteria including monocopy applications. Gene 196: 69-74.

Taso, S. G. S., et al. (1983). Hybridization of nucleic acids directly in agarose gels. Anal. Biochem. 131: 365-372.

Umelo-Njaka, E., et al. (2000). Expression and testing of *Pseudomonas aeruginosa* vaccine candidate proteins prepared with the *Caulobacter crescentus* S-layer protein expression system. Vaccine 19: 1406-1415.

Vieira, J. and Messing, J. (1982). The pUC plasmids, an M13mp7-derived system for insertion mutagenesis and sequencing with synthetic universal primers. Gene 19: 259-268.

Walker, S. G., et al. (1994). Characterization of mutants of *Caulobacter crescentus* defective in surface attachment of the paracrystalline surface layer. J. Bacteriol. 176: 6312-6323.

Walker, S. G., et al. (1992). Isolation and comparison of the paracrystalline surface layer proteins of freshwater caulobacters. J. Bacteriol. 174: 1783-1792.

Yanisch-Perron, C., et al. (1985). Improved M13 cloning vectors and host strains: Nucleotide sequences of the M13mp18 and pUC19 vectors. Gene 33: 103-119.

Xu, L., Mourich, et al. (1991). Epitope mapping and characterization of the infectious hematopoietic necrosis virus glycoprotein using fusion proteins synthesized in *Escherichia coli*. J. Virol. 65: 1611-1615.

We claim:

1. An isolated *Caulobacter* deficient in a protease native to *Caulobacter* that cleaves hybrid *Caulobacter* S-layer protein monomers, wherein said protease comprises an amino acid sequence having at least 95% identity with the amino acid sequence set forth in SEQ ID NO:3.

2. The isolated *Caulobacter* of claim 1, wherein said protease comprises a metalloprotease active site.

3. The isolated *Caulobacter* of claim 1 or claim 2, wherein said protease comprises at least one $Ca^{++}$-binding sequence as set forth in SEQ ID NO.5.

4. The isolated *Caulobacter* of claim 1, wherein the amino acid sequence of said protease comprises a region of at least 190 amino acids in the C-terminal portion of said protease commencing at a position equivalent to position 451 of SEQ ID NO:3 and having 30% or more sequence identity to a region of at least 190 amino acids in the N-terminal portion of a *Caulobacter* S-layer protein monomer set forth in SEQ ID NO:1.

5. The isolated *Caulobacter* of claim 4, wherein said region in the C-terminal portion of said protease comprises from 190 to 230 amino acids.

6. The isolated *Caulobacter* of claim 4, wherein said region in the N-terminal portion of said S-layer protein monomer comprises the sequence of amino acids from position 23 to position 242 of SEQ ID NO:1.

7. The isolated *Caulobacter* of claim 6, wherein said region in the C-terminal portion of said protease comprises a sequence of at least 200 amino acids.

8. The isolated *Caulobacter* of claim 1, wherein said protease comprises the amino acid sequence set forth in SEQ ID NO:3.

9. The isolated *Caulobacter* according to claim 1, wherein the isolated *Caulobacter* is deficient in the activity of said protease as a result of a deletion, substitution, or addition of at least one nucleotide in a gene encoding the protease.

10. The isolated *Caulobacter* of claim 1, wherein the isolated *Caulobacter* comprises a recombinant DNA capable of expression of a hybrid S-layer protein monomer and is incapable of secreting an S-layer protein monomer encoded by the endogenous S-layer protein gene of said *Caulobacter*.

11. The isolated *Caulobacter* of claim 10, wherein the hybrid S-layer protein monomer secreted by the isolated *Caulobacter* is capable of attachment to the cell surface of a *Caulobacter*, and comprises one or more peptides heterologous to a *Caulobacter* S-layer protein monomer.

12. A library of *Caulobacter* in which members of the library are different isolated *Caulobacter* according to claim 11, wherein the hybrid S-layer protein monomers of the members differ by comprising amino acid sequences of one or more peptides heterologous to a *Caulobacter* S-layer protein monomer.

13. A method of sorting a library of claim 12 according to the ability of a heterologous peptide to bind to a target, comprising exposing the library to the target, and separating members of the library that bind to the target from members which do not bind to the target.

14. The method of claim 13, wherein the target is labelled and the presence of the label bound to a member is indicative of binding of the target to the member.

15. The method of claim 14, wherein the label is fluorescent and the separation is performed by a flow cytometer.

16. A method of producing a *Caulobacter* optimized for use as a host cell for expression of a hybrid *Caulobacter* S-layer protein monomer, comprising:
  i) providing a *Caulobacter* which exhibits protease activity whereby hybrid S-layer protein monomers expressed by the *Caulobacter* are cleaved;
  ii) mutating the *Caulobacter*, and
  iii) selecting and culturing a mutated *Caulobacter* which does not exhibit said protease activity.

17. The method of claim 16, wherein the *Caulobacter* is mutated by introduction into the *Caulobacter* of a nucleic acid capable of homologous recombination with all or a part of SEQ ID NO: 2.

18. The method of claim 16, wherein the *Caulobacter* is mutated by transposon insertion.

19. The method of claim 16, wherein the *Caulobacter* is mutated by one or more of radiation and a chemical mutagen.

20. The method of claim 16, wherein the Caulobacter which exhibits protease activity expresses a protein comprising an amino acid sequence having at least 95% sequence identity to SEQ ID NO: 3, and the *Caulobacter* is mutated so as to result in insertion, deletion, or substitution of at least one amino acid in said amino acid sequence.

21. A mutated *Caulobacter* or descendents thereof, produced by the method of claim 16 and which does not exhibit a protease activity whereby hybrid S-layer protein monomers are cleaved.

22. A library of mutated *Caulobacter* or descendents thereof of claim 21, wherein members of the library express and secrete different hybrid *Caulobacter* S-layer protein monomers.

23. A method of sorting the library of claim 22 according to the ability for the different hybrid S-layer protein monomers to bind a target, comprising exposing the library to the target, and separating members of the library that bind to the target from members which do not bind to the target.

24. The method of claim 23, wherein the target is labelled and presence of the label bound to a member is indicative of binding of the target to the member.

25. The method of claim 24, wherein the label is fluorescent and the separation is performed by a flow cytometer.

26. A method of sorting members of a *Caulobacter* library according to the ability of a hybrid S-layer monomer protein on a *Caulobacter* to bind to a target, wherein said members of the library are deficient in a protease native to *Caulo-*

*bacter* that cleaves hybrid *Caulobacter* S-layer protein monomers, said protease comprises an amino acid sequence having at least 95% identity with the amino acid sequence set forth in SEQ ID NO:3, and wherein said members express and secrete different hybrid S-layer protein monomers, comprising:

i) exposing the library to a fluorescent labeled target; and
ii) segregating members of the library with a flow cytometer according to whether the labeled target is bound to a member or is not bound to a member.

* * * * *

SEQUENCE LISTING

```
<160> NUMBER OF SEQ ID NOS: 6

<210> SEQ ID NO 1
<211> LENGTH: 1026
<212> TYPE: PRT
<213> ORGANISM: Caulobacter crescentus

<400> SEQUENCE: 1

Met Ala Tyr Thr Thr Ala Gln Leu Val Thr Ala Tyr Thr Asn Ala Asn
```

```
              1               5                  10                 15
        Leu Gly Lys Ala Pro Asp Ala Ala Thr Thr Leu Thr Leu Asp Ala Tyr
                         20                 25                 30

Ala Thr Gln Thr Gln Thr Gly Gly Leu Ser Asp Ala Ala Leu Thr
                     35                 40                 45

Asn Thr Leu Lys Leu Val Asn Ser Thr Thr Ala Val Ala Ile Gln Thr
                     50                 55                 60

Tyr Gln Phe Phe Thr Gly Val Ala Pro Ser Ala Ala Gly Leu Asp Phe
        65                  70                 75                 80

Leu Val Asp Ser Thr Thr Asn Thr Asn Asp Leu Asn Asp Ala Tyr Tyr
                         85                 90                 95

Ser Lys Phe Ala Gln Glu Asn Arg Phe Ile Asn Phe Ser Ile Asn Leu
                     100                105                110

Ala Thr Gly Ala Gly Ala Gly Ala Thr Ala Phe Ala Ala Ala Tyr Thr
                     115                120                125

Gly Val Ser Tyr Ala Gln Thr Val Ala Thr Ala Tyr Asp Lys Ile Ile
                     130                135                140

Gly Asn Ala Val Ala Thr Ala Ala Gly Val Asp Val Ala Ala Ala Val
        145                 150                155                160

Ala Phe Leu Ser Arg Gln Ala Asn Ile Asp Tyr Leu Thr Ala Phe Val
                     165                170                175

Arg Ala Asn Thr Pro Phe Thr Ala Ala Asp Ile Asp Leu Ala Val
                     180                185                190

Lys Ala Ala Leu Ile Gly Thr Ile Leu Asn Ala Ala Thr Val Ser Gly
                     195                200                205

Ile Gly Gly Tyr Ala Thr Ala Thr Ala Ala Met Ile Asn Asp Leu Ser
                     210                215                220

Asp Gly Ala Leu Ser Thr Asp Asn Ala Ala Gly Val Asn Leu Phe Thr
        225                 230                235                240

Ala Tyr Pro Ser Ser Gly Val Ser Gly Ser Thr Leu Ser Leu Thr Thr
                     245                250                255

Gly Thr Asp Thr Leu Thr Gly Thr Ala Asn Asn Asp Thr Phe Val Ala
                     260                265                270

Gly Glu Val Ala Gly Ala Ala Thr Leu Thr Val Gly Asp Thr Leu Ser
                     275                280                285

Gly Gly Ala Gly Thr Asp Val Leu Asn Trp Val Gln Ala Ala Ala Val
                     290                295                300

Thr Ala Leu Pro Thr Gly Val Thr Ile Ser Gly Ile Glu Thr Met Asn
        305                 310                315                320

Val Thr Ser Gly Ala Ala Ile Thr Leu Asn Thr Ser Ser Gly Val Thr
                     325                330                335

Gly Leu Thr Ala Leu Asn Thr Asn Thr Ser Gly Ala Ala Gln Thr Val
                     340                345                350

Thr Ala Gly Ala Gly Gln Asn Leu Thr Ala Thr Ala Ala Gln Ala
                     355                360                365

Ala Asn Asn Val Ala Val Asp Gly Gly Ala Asn Val Thr Val Ala Ser
                     370                375                380

Thr Gly Val Thr Ser Gly Thr Thr Val Gly Ala Asn Ser Ala Ala
        385                 390                395                400

Ser Gly Thr Val Ser Val Ser Val Ala Asn Ser Ser Thr Thr Thr Thr
                     405                410                415

Gly Ala Ile Ala Val Thr Gly Gly Thr Ala Val Thr Val Ala Gln Thr
                     420                425                430
```

-continued

```
Ala Gly Asn Ala Val Asn Thr Thr Leu Thr Gln Ala Asp Val Thr Val
            435                 440                 445
Thr Gly Asn Ser Ser Thr Thr Ala Val Thr Val Thr Gln Thr Ala Ala
        450                 455                 460
Ala Thr Ala Gly Ala Thr Val Ala Gly Arg Val Asn Gly Ala Val Thr
465                 470                 475                 480
Ile Thr Asp Ser Ala Ala Ser Ala Thr Thr Ala Gly Lys Ile Ala
                485                 490                 495
Thr Val Thr Leu Gly Ser Phe Gly Ala Ala Thr Ile Asp Ser Ser Ala
                500                 505                 510
Leu Thr Thr Val Asn Leu Ser Gly Thr Gly Thr Ser Leu Gly Ile Gly
                515                 520                 525
Arg Gly Ala Leu Thr Ala Thr Pro Thr Ala Asn Thr Leu Thr Leu Asn
            530                 535                 540
Val Asn Gly Leu Thr Thr Thr Gly Ala Ile Thr Asp Ser Glu Ala Ala
545                 550                 555                 560
Ala Asp Asp Gly Phe Thr Thr Ile Asn Ile Ala Gly Ser Thr Ala Ser
                565                 570                 575
Ser Thr Ile Ala Ser Leu Val Ala Ala Asp Ala Thr Thr Leu Asn Ile
                580                 585                 590
Ser Gly Asp Ala Arg Val Thr Ile Thr Ser His Thr Ala Ala Ala Leu
            595                 600                 605
Thr Gly Ile Thr Val Thr Asn Ser Val Gly Ala Thr Leu Gly Ala Glu
        610                 615                 620
Leu Ala Thr Gly Leu Val Phe Thr Gly Gly Ala Gly Ala Asp Ser Ile
625                 630                 635                 640
Leu Leu Gly Ala Thr Thr Lys Ala Ile Val Met Gly Ala Gly Asp Asp
                645                 650                 655
Thr Val Thr Val Ser Ser Ala Thr Leu Gly Ala Gly Gly Ser Val Asn
                660                 665                 670
Gly Gly Asp Gly Thr Asp Val Leu Val Ala Asn Val Asn Gly Ser Ser
            675                 680                 685
Phe Ser Ala Asp Pro Ala Phe Gly Gly Phe Glu Thr Leu Arg Val Ala
        690                 695                 700
Gly Ala Ala Ala Gln Gly Ser His Asn Ala Asn Gly Phe Thr Ala Leu
705                 710                 715                 720
Gln Leu Gly Ala Thr Ala Gly Ala Thr Thr Phe Thr Asn Val Ala Val
                725                 730                 735
Asn Val Gly Leu Thr Val Leu Ala Ala Pro Thr Gly Thr Thr Thr Val
                740                 745                 750
Thr Leu Ala Asn Ala Thr Gly Thr Ser Asp Val Phe Asn Leu Thr Leu
            755                 760                 765
Ser Ser Ser Ala Ala Leu Ala Ala Gly Thr Val Ala Leu Ala Gly Val
        770                 775                 780
Glu Thr Val Asn Ile Ala Ala Thr Asp Thr Asn Thr Ala His Val
785                 790                 795                 800
Asp Thr Leu Thr Leu Gln Ala Thr Ser Ala Lys Ser Ile Val Val Thr
                805                 810                 815
Gly Asn Ala Gly Leu Asn Leu Thr Asn Thr Gly Asn Thr Ala Val Thr
                820                 825                 830
Ser Phe Asp Ala Ser Ala Val Thr Gly Thr Gly Ser Ala Val Thr Phe
            835                 840                 845
```

-continued

```
     Val Ser Ala Asn Thr Thr Val Gly Glu Val Val Thr Ile Arg Gly Gly
         850                 855                 860

Ala Gly Ala Asp Ser Leu Thr Gly Ser Ala Thr Ala Asn Asp Thr Ile
 865                 870                 875                 880

Ile Gly Gly Ala Gly Ala Asp Thr Leu Val Tyr Thr Gly Gly Thr Asp
                     885                 890                 895

Thr Phe Thr Gly Gly Thr Gly Ala Asp Ile Phe Asp Ile Asn Ala Ile
                 900                 905                 910

Gly Thr Ser Thr Ala Phe Val Thr Ile Thr Asp Ala Ala Val Gly Asp
             915                 920                 925

Lys Leu Asp Leu Val Gly Ile Ser Thr Asn Gly Ala Ile Ala Asp Gly
         930                 935                 940

Ala Phe Gly Ala Ala Val Thr Leu Gly Ala Ala Ala Thr Leu Ala Gln
 945                 950                 955                 960

Tyr Leu Asp Ala Ala Ala Gly Asp Gly Ser Gly Thr Ser Val Ala
                     965                 970                 975

Lys Trp Phe Gln Phe Gly Gly Asp Thr Tyr Val Val Asp Ser Ser
                 980                 985                 990

Ala Gly Ala Thr Phe Val Ser Gly Ala Asp Ala Val Ile Lys Leu Thr
             995                 1000                1005

Gly Leu Val Thr Leu Thr Thr Ser Ala Phe Ala Thr Glu Val Leu
         1010                1015                1020

Thr Leu Ala
         1025

<210> SEQ ID NO 2
<211> LENGTH: 2270
<212> TYPE: DNA
<213> ORGANISM: Caulobacter crescentus

<400> SEQUENCE: 2
catttgaaaa ccctttttct acgaaagtcg cggacccgac atcttgcctg ggacctgcag    60
cacaaacgcg ccatgcgagc atttagctgt ggcgcctggg caacaaagtg agttggaagc   120
tgaaaaaggt gacgaaggcc accccgccaa ggtctggctc cgcccgagcg agcgctgtgc   180
gaacttgtcg caaatagcca agattgcaga agaaattctg cttctccata ctcctttcag   240
gtgagtggag cgcgtcggtg tgtagtcagt gcgagcggta tggactgaac ctccacgggg   300
atgatgtcgc cccggccgtc tcgggtggcg agggtcccta cgcgtttgtc gacgccgact   360
tgctgcgcag cgagccgggc tggtcgaacc agttcctggt ccccgcgacc gtgacctatg   420
cgttccgcgc gaccgcaccg gcgagcatgc ccagcgatac gggcggcttt tcgcagttca   480
acgccgccca gatcctccag gccgagaagg cgctgcaggc tggtccgac gtcgccaaca   540 tcacctttgt ccgcgtgggc cagggcacgt cgggcgaggc cgcctacagc gacaacgcct   600
cgatcctgtt cgccaatttc agcaccggca gcgagggctc ggcgggcttc gcctactatc   660
cgggcaaccc tgcggccagc agccggtccg gcgatgtctg gatcaagtcg acggccggct   720
acaacaccaa cccgaccggc tccaactatg cggcatggt gctggttcac gagctggggc   780
acgccatcgg catcgcccac cccagcgagt acaacgccag cgccgacgac accctgacct   840
atgcggtcaa cgcgacctac taccaggaca gccgccagta cacggtaatg tcctatttca   900
gcgaggccaa caccggcggc tcgttcggcg gcgcctacgc ctcctcgccc ctgctcgatg   960
acatcgccgc cgcccagttg gcctatggcg ccaacatgac cacgcgcacc ggcgacacgg  1020
tgtacggctt caactcgacc gccggccgcg agtggttcgc ggcgacctcg tcctcgaccc  1080
```

-continued

```
ggctggtgtt cgcggtctgg gacgccggcg gcgtcgacac cctggacttc tccggctatc   1140
gcgtggccca gaccatcgac ctgcgagcag gctatttctc cagcgtcggc ggcctgaagg   1200
gcaatgtcac catcgccatg aacgcggtga tcgagaacgc catcggcggc tcggcggccg   1260
acaccatcaa cggaaacgct gtcgacaacc ggctgaccgg cggcgcgggc gccgacatcc   1320
tggacggcgg ccggggcgtc gacaccgccg tcttctccgg cgcctacggc aactacaccc   1380
tgaccgccgc cacgaacggc gcctggtcgg tgctcgaccg ggtggggacg gacgccaccg   1440
ataccctggc gaacatcgag ttcctggcct ttaccgatcg gaccgtgacg ctcgtcgaca   1500
gccgcgtcgc gaccgcgatc agcaatatcc tgcgcctgca gaccttcagc gcctcggccg   1560
aaccgctgtc caagagcctg gcggcctcga tggccgccgg cgccagccat agcgacgcca   1620
tcggccaggt gtccaagacc gcgctgtcga ccagcggggt ggcggtgctg gcctatcagt   1680
tcttcaccgg caagacgccc acggcggccg gcatggatta tctggtcaat ccggacggcg   1740
tgaacgccaa caacctcaac agcgcctact atcagtcgtt caatctcgag aaccgctaca   1800
tcaacttcgc ggtcaatctg gcaagatcg gcgagggagc caccaagttc ctggccgact   1860
atggcgggct cagcctgttt gacgccacgc gcaaggccta tgcgaccatc tttggcctga   1920
cgccaccga cgacaaggtg cgcgccctga tcgacggccg caccgactac ttcgccgcct   1980
atggccagga cgggccaaac ggccagggaa ccaaggcggc catggtgggc tggctgatgg   2040
ccgaggcggg caaggccgac atcggcgtct acgccaagtc ggcgggggcc ttcttcgccg   2100
accaggccac caagaatgtc tatggcgtgg atctgatcgg cgtctacgcc aagccggaat   2160
acaacctcat ctgaccgttc gaagggcgcg gcgacaaagg tccagacagc gatttgaagg   2220
gagtaagggc gggcggccct ccccgaaaa ggtcgccgcc cgagttgctt              2270
```

<210> SEQ ID NO 3
<211> LENGTH: 658
<212> TYPE: PRT
<213> ORGANISM: Caulobacter crescentus

<400> SEQUENCE: 3

```
Met Cys Ser Gln Cys Glu Arg Tyr Gly Leu Asn Leu His Gly Asp Asp
1               5                   10                  15

Val Ala Pro Ala Val Ser Gly Gly Glu Gly Pro Tyr Ala Phe Val Asp
            20                  25                  30

Ala Asp Ser Arg Val Gly Thr Val Asp Gly Lys Lys Ser Leu Thr Val
        35                  40                  45

Pro Glu Ala Ala Leu Gln Leu Leu Arg Ser Glu Pro Gly Trp Ser Asn
    50                  55                  60

Gln Phe Leu Val Pro Ala Thr Val Thr Tyr Ala Phe Arg Ala Thr Ala
65                  70                  75                  80

Pro Ala Ser Met Pro Ser Asp Thr Gly Gly Phe Ser Gln Phe Asn Ala
                85                  90                  95

Ala Gln Ile Leu Gln Ala Glu Lys Ala Leu Gln Ala Trp Ser Asp Val
            100                 105                 110

Ala Asn Ile Thr Phe Val Arg Val Gly Gln Gly Thr Ser Gly Glu Ala
        115                 120                 125

Ala Tyr Ser Asp Asn Ala Ser Ile Leu Phe Ala Asn Phe Ser Thr Gly
    130                 135                 140

Ser Glu Gly Ser Ala Gly Phe Ala Tyr Tyr Pro Gly Asn Pro Ala Ala
145                 150                 155                 160
```

-continued

```
Ser Ser Arg Ser Gly Asp Val Trp Ile Lys Ser Thr Ala Gly Tyr Asn
            165                 170                 175

Thr Asn Pro Thr Gly Ser Asn Tyr Gly Gly Met Val Leu Val His Glu
        180                 185                 190

Leu Gly His Ala Ile Gly Ile Ala His Pro Ser Glu Tyr Asn Ala Ser
        195                 200                 205

Ala Asp Asp Thr Leu Thr Tyr Ala Val Asn Ala Thr Tyr Tyr Gln Asp
    210                 215                 220

Ser Arg Gln Tyr Thr Val Met Ser Tyr Phe Ser Glu Ala Asn Thr Gly
225                 230                 235                 240

Gly Ser Phe Gly Gly Ala Tyr Ala Ser Ser Pro Leu Leu Asp Asp Ile
                245                 250                 255

Ala Ala Ala Gln Leu Ala Tyr Gly Ala Asn Met Thr Thr Arg Thr Gly
            260                 265                 270

Asp Thr Val Tyr Gly Phe Asn Ser Thr Ala Gly Arg Glu Trp Phe Ala
        275                 280                 285

Ala Thr Ser Ser Ser Thr Arg Leu Val Phe Ala Val Trp Asp Ala Gly
        290                 295                 300

Gly Val Asp Thr Leu Asp Phe Ser Gly Tyr Arg Val Ala Gln Thr Ile
305                 310                 315                 320

Asp Leu Arg Ala Gly Tyr Phe Ser Ser Val Gly Gly Leu Lys Gly Asn
                325                 330                 335

Val Thr Ile Ala Met Asn Ala Val Ile Glu Asn Ala Ile Gly Gly Ser
            340                 345                 350

Ala Ala Asp Thr Ile Asn Gly Asn Ala Val Asp Asn Arg Leu Thr Gly
        355                 360                 365

Gly Ala Gly Ala Asp Ile Leu Asp Gly Gly Arg Gly Val Asp Thr Ala
    370                 375                 380

Val Phe Ser Gly Ala Tyr Gly Asn Tyr Thr Leu Thr Ala Ala Thr Asn
385                 390                 395                 400

Gly Ala Trp Ser Val Leu Asp Arg Val Gly Thr Asp Ala Thr Asp Thr
                405                 410                 415

Leu Ala Asn Ile Glu Phe Leu Ala Phe Thr Asp Arg Thr Val Thr Leu
            420                 425                 430

Val Asp Ser Arg Val Ala Thr Ala Ile Ser Asn Ile Leu Arg Leu Gln
        435                 440                 445

Thr Phe Ser Ala Ser Ala Glu Pro Leu Ser Lys Ser Leu Ala Ala Ser
    450                 455                 460

Met Ala Ala Gly Ala Ser His Ser Asp Ala Ile Gly Gln Val Ser Lys
465                 470                 475                 480

Thr Ala Leu Ser Thr Ser Gly Val Ala Val Leu Ala Tyr Gln Phe Phe
                485                 490                 495

Thr Gly Lys Thr Pro Thr Ala Ala Gly Met Asp Tyr Leu Val Asn Pro
            500                 505                 510

Asp Gly Val Asn Ala Asn Asn Leu Asn Ser Ala Tyr Tyr Gln Ser Phe
        515                 520                 525

Asn Leu Glu Asn Arg Tyr Ile Asn Phe Ala Val Asn Leu Gly Lys Ile
    530                 535                 540

Gly Glu Gly Ala Thr Lys Phe Leu Ala Asp Tyr Gly Leu Ser Leu
545                 550                 555                 560

Phe Asp Ala Thr Arg Lys Ala Tyr Ala Thr Ile Phe Gly Leu Thr Pro
                565                 570                 575

Thr Asp Asp Lys Val Arg Ala Leu Ile Asp Gly Arg Thr Asp Tyr Phe
```

```
                    580                 585                 590
Ala Ala Tyr Gly Gln Asp Gly Pro Asn Gly Gln Gly Thr Lys Ala Ala
            595                 600                 605

Met Val Gly Trp Leu Met Ala Glu Ala Gly Lys Ala Asp Ile Gly Val
    610                 615                 620

Tyr Ala Lys Ser Ala Gly Ala Phe Phe Ala Asp Gln Ala Thr Lys Asn
625                 630                 635                 640

Val Tyr Gly Val Asp Leu Ile Gly Val Tyr Ala Lys Pro Glu Tyr Asn
                645                 650                 655

Leu Ile

<210> SEQ ID NO 4
<211> LENGTH: 11
<212> TYPE: PRT
<213> ORGANISM: Caulobacter crescentus
<220> FEATURE:
<221> NAME/KEY: misc_feature
<222> LOCATION: (3)..(3)
<223> OTHER INFORMATION: Xaa = an arbitrary amino acid
<220> FEATURE:
<221> NAME/KEY: misc_feature
<222> LOCATION: (4)..(4)
<223> OTHER INFORMATION: Xaa = an arbitrary amino acid
<220> FEATURE:
<221> NAME/KEY: misc_feature
<222> LOCATION: (6)..(6)
<223> OTHER INFORMATION: Xaa = an arbitrary amino acid
<220> FEATURE:
<221> NAME/KEY: misc_feature
<222> LOCATION: (7)..(7)
<223> OTHER INFORMATION: Xaa = a bulky hydrophobic residue
<220> FEATURE:
<221> NAME/KEY: misc_feature
<222> LOCATION: (9)..(9)
<223> OTHER INFORMATION: Xaa = a bulky hydrophobic residue
<220> FEATURE:
<221> NAME/KEY: misc_feature
<222> LOCATION: (10)..(10)
<223> OTHER INFORMATION: Xaa = an arbitrary amino acid

<400> SEQUENCE: 4

His Glu Xaa Xaa His Xaa Xaa Gly Xaa Xaa His
1               5                   10

<210> SEQ ID NO 5
<211> LENGTH: 6
<212> TYPE: PRT
<213> ORGANISM: Caulobacter crescentus
<220> FEATURE:
<221> NAME/KEY: misc_feature
<222> LOCATION: (3)..(3)
<223> OTHER INFORMATION: Xaa = an arbitrary residue
<220> FEATURE:
<221> NAME/KEY: misc_feature
<222> LOCATION: (5)..(5)
<223> OTHER INFORMATION: Xaa = an arbitrary residue

<400> SEQUENCE: 5

Gly Gly Xaa Gly Xaa Asp
1               5

<210> SEQ ID NO 6
<211> LENGTH: 20
<212> TYPE: PRT
<213> ORGANISM: Infectious hematopoietic necrosis virus
```

```
<400> SEQUENCE: 6

Ala Ser Glu Ser Arg Glu Glu Leu Leu Glu Ala His Ala Glu Ile Ile
1               5                   10                  15

Ser Thr Asn Ser
            20
```